US008762066B2

(12) United States Patent
Fox

(10) Patent No.: US 8,762,066 B2
(45) Date of Patent: Jun. 24, 2014

(54) METHODS, SYSTEMS, AND SOFTWARE FOR IDENTIFYING FUNCTIONAL BIOMOLECULES

(75) Inventor: Richard John Fox, Kirkwood, MO (US)

(73) Assignee: Codexis Mayflower Holdings, LLC, Redwood City, CA (US)

( * ) Notice: Subject to any disclaimer, the term of this patent is extended or adjusted under 35 U.S.C. 154(b) by 1578 days.

(21) Appl. No.: 11/981,578

(22) Filed: Oct. 30, 2007

(65) Prior Publication Data
US 2008/0132416 A1 Jun. 5, 2008

Related U.S. Application Data

(63) Continuation of application No. 10/874,802, filed on Jun. 22, 2004, now abandoned, which is a continuation-in-part of application No. 10/629,351, filed on Jul. 29, 2003, now Pat. No. 7,747,391, which is a continuation-in-part of application No. 10/379,378, filed on Mar. 3, 2003, now Pat. No. 7,783,428.

(60) Provisional application No. 60/360,982, filed on Mar. 1, 2002.

(51) Int. Cl.
*G01N 33/48* (2006.01)
*G06G 7/48* (2006.01)
*G06F 19/18* (2011.01)
*G06F 19/24* (2011.01)
*G06F 19/22* (2011.01)

(52) U.S. Cl.
CPC ............... *G06F 19/18* (2013.01); *G06F 19/24* (2013.01); *G06F 19/22* (2013.01)
USPC .............................................. 702/19; 703/11

(58) Field of Classification Search
None
See application file for complete search history.

(56) References Cited

U.S. PATENT DOCUMENTS

| | | | |
|---|---|---|---|
| 6,117,679 A | 9/2000 | Stemmer | |
| 6,376,246 B1 | 4/2002 | Crameri et al. | |
| 6,537,776 B1 | 3/2003 | Short | |
| 6,586,182 B1 | 7/2003 | Patten et al. | |
| 6,605,449 B1 | 8/2003 | Short | |
| 7,315,786 B2 | 1/2008 | Dahiyat et al. | |
| 7,747,391 B2 | 6/2010 | Gustafsson et al. | |
| 7,747,393 B2 | 6/2010 | Fox | |
| 7,751,986 B2 | 7/2010 | Gustafsson et al. | |
| 7,783,428 B2 | 8/2010 | Gustafsson et al. | |
| 7,991,557 B2 | 8/2011 | Liew et al. | |
| 2001/0051855 A1 | 12/2001 | Wang et al. | |
| 2002/0045175 A1 | 4/2002 | Wang et al. | |
| 2002/0048772 A1 | 4/2002 | Dahiyat et al. | |
| 2002/0155460 A1 | 10/2002 | Schellenberger et al. | |
| 2003/0032059 A1 | 2/2003 | Wang et al. | |
| 2004/0072245 A1 | 4/2004 | Gustafsson et al. | |
| 2004/0161796 A1 | 8/2004 | Gustafsson et al. | |
| 2005/0084907 A1 | 4/2005 | Fox | |
| 2006/0205003 A1 | 9/2006 | Gustafsson et al. | |
| 2007/0239364 A1 | 10/2007 | Fox | |
| 2008/0133143 A1 | 6/2008 | Gustafsson et al. | |
| 2008/0147369 A1 | 6/2008 | Fox | |
| 2008/0220990 A1 | 9/2008 | Fox | |
| 2009/0312196 A1 | 12/2009 | Colbeck et al. | |
| 2010/0004135 A1 | 1/2010 | Fox | |
| 2010/0004136 A1 | 1/2010 | Fox | |
| 2010/0005047 A1 | 1/2010 | Fox | |
| 2011/0257023 A1 | 10/2011 | Gustafsson et al. | |

FOREIGN PATENT DOCUMENTS

| | | |
|---|---|---|
| JP | 2002-534965 | 10/2002 |
| JP | 2003-521933 | 7/2003 |
| JP | 2005-519384 | 6/2005 |
| WO | WO 00/42560 | 7/2000 |
| WO | WO01/59066 | 8/2001 |
| WO | WO01/61344 | 8/2001 |
| WO | WO03/055978 | 7/2003 |
| WO | WO 03/075129 | 9/2003 |
| WO | WO 03/085548 | 10/2003 |
| WO | WO 2006/002267 | 1/2006 |

OTHER PUBLICATIONS

Berglund et al., "INLR, Implicit non-linear latent variable regression," Journal of Chemometrics, vol. 11 (1997) pp. 141-156.*
Gribskov et al., "Profile analysis: Detection of distantly related proteins," vol. 84 (1987) pp. 4355-4358.*
Goodacre et al., "Detection of the Dipicolinic Acid Biomarker in *Bacillus* Spores Using Curie-Point Pyrolysis Mass Spectrometry and Fourier Transform Infrared Spectroscopy," *Anal. Chem.* (2000), 72, 119-127.
Geladi et al., "Partial Least-Squares Regression: A Tutorial," *Analytica Chimica Acta*, 185 (1986) 1-17.
The GMAX: printed from website http://www.abergc.com, prior to Jul. 21, 2003, 3 pages.
Steve R. Gunn, "Support Vector Machines for Classification and Regression," Technical Report, Department of Electronics and Computer Science, University of Southampton, 1998, 57 Pages.

(Continued)

*Primary Examiner* — Anna Skibinsky
(74) *Attorney, Agent, or Firm* — Weaver Austin Villeneuve & Sampson LLP

(57) ABSTRACT

The present invention generally relates to methods of rapidly and efficiently searching biologically-related data space. More specifically, the invention includes methods of identifying bio-molecules with desired properties, or which are most suitable for acquiring such properties, from complex bio-molecule libraries or sets of such libraries. The invention also provides methods of modeling sequence-activity relationships. As many of the methods are computer-implemented, the invention additionally provides digital systems and software for performing these methods.

31 Claims, 10 Drawing Sheets

(56) References Cited

OTHER PUBLICATIONS

Voigt et al., "Rational Evolutionary Design: The Theory of In Vitro Protein Evolution," Advances in Protein Chemistry, Academic Press, vol. 55, pp. 79-160, 2001.

Dahiyat et al., "De Novo Protein Design: Fully Automated Sequence Selection," Science, American Assoc fro the Advancement of Science, vol. 278, No. 5335, p. 82-87, 1997.

Fox et al., "Optimizing the Search Algorithm for Protein Engineering by Directed Evolution," Protein Engineering, Oxford Univ Press, vol. 16, No. 8, pp. 589-597, 2003.

Supplemental Partial EPO Search Report for Int'l Application No. PCT/US03/06551, dated Nov. 28, 2005, 6 pages.

Skibinsky, "Office Action for U.S. Appl. No. 10/379,378" mailed Sep. 28, 2006.

U.S. Office Action mailed Mar. 13, 2006, from U.S. Appl. No. 10/379,378.

U.S. Office Action mailed Jan. 27, 2006, from U.S. Appl. No. 10/386,903.

Eroshkin et al., "PROANAL version 2: Multifunctional Program for Analysis of Multiple Protein Sequence Alignments and for Studying the Structure-Activity Relationships in Protein Families," Comput. Appl. Biosci., vol. 11, No. 1, pp. 39-44, 1995.

Eroshkin et al., "Algortihm and Computer Program Pro_Anal for Analysis of Relationship Between Structure and Activity in a Family of Proteins or Peptides," Comput. Appl. Biosci., vol. 9, No. 5, pp. 491-497, 1993.

Ivanisenko,V.A. and Eroshkin,A.M, "Search for Sites With Functionally Important Substitutions in Sets of Related or Mutant Protein," Mol. Biol. (Moskow), 31, pp. 749-755, 1997.

Hellberg et al., "The Prediction of Bradykinin Potentiating Potency of Pentapeptides. An Example of a Peptide Quantitative Structure-Activity Relationship," Acia Chemica Scandinaviea B 40, pp. 135-140, 1988.

Bucht et al., "Optimising the Signal Peptide for Glycosyl Phosphatidylinositol Modification of Human Acetylcholinesterase Using Mutational Analysis and Peptide-Quantitative Structure-Activity Relationships," Biochimica et Biophysica Acta 1431, pp. 471-482, 1999.

Sandberg et al., "Engineering Multiple Properties of a Protein by Combinatorial Mutagenesis," Proc. Natl. Acad. Sci. USA, vol. 90, pp. 8367-8371, Sep. 1993.

Wrede et al., "Peptide Design Aided by Neural Networks: Biological Activity of Artificial Signal Peptidase I Cleavage Sites," Biochemistry, 37, pp. 3588-3593, 1998.

Jill Damborsky, "Quantitative Structure-Function and Structure-Stability Relationships of Purposely Modified Proteins," Protein Engineering, vol. 11, No. 1, pp. 21-30, 1998.

Hellberg, et al., "Peptide Quantitative Structure—Activity Relationships, a Multivariate Approach," J. Med Chem, 30: pp. 1126-1195, 1987.

Sandberg et al., "New Chemical Descriptors Relevant for the Design of Biologically Active Peptides. A Multivariate Characterization of 87 Amino Acids," J. Med Chem., 41, pp. 2481-2491, 1998.

Casari et al., "A Method to Predict Functional Residues in Proteins," Nat. Struct Biol., 2, pp. 171-178, 1995.

Suzuki et al., "A Method for Detecting Positive Selection at Single Amino Acid Sites," Mol. Biol. Evol. 16 (10): pp. 1315-1328, 1999.

Benner et al., "Amino Acid Substitution During Functionally Constrained Divergent Evolution of Protein Sequences," Protein Engineering, vol. 7, No. 11, pp. 1323-1332, 1994.

Wu et al., "Discovering Empirically Conserved Amino Acid Substitution Groups in Databases of Protein Families," Proc. Int. Conf. Intell. Syst. Mol. Biol., 4, pp. 230-240, 1996.

Adenot et al., "Peptides Quantitative Structure-Function Relationships: an Automated Mutation Strategy to Design Peptides and Pseudopeptides from Substitution Matrices," Journal of Molecular Graphics and Modelling, 17, pp. 292-309, 1999.

Norinder et al., "A Quantitative Structure-Activity Relationship Study of Some Substance P-Related Peptides," J. Peptide Res., 49, pp. 155-162, 1997.

Sandberg, "Deciphering Sequence Data a Multivariate Approach," Ph.D Thesis, Umea: Umea University, 78 pages, 1997.

Eriksson et al., "Peptide QSAR on Substance P Analogues, Enkephalins and Bradykinins Containing L-and D-Amino Acids," Acta Chemica Scandinavica, 44, pp. 50-56, 1990.

Ufkes eta l., "Further Studies on the Structure-Activity Relationships of Bradykinin-Potentiating Peptides," European Journal of Pharmacology, 79, pp. 155-158, 1982.

Dobrynin et al., "Synthesis of Model Promoter for Gene Expression in *Escherichia Coli*," Symposium Series No. 7, pp. 365-376, 1980.

Skinner et al., "Potential Use of Additivity of Mutational Effects in Simplifying Protein Engineering," Proc. Natl. Acad. Sci., vol. 93, pp. 10753-10757, 1996.

Lathrop et al., "Global Optimum Protein Threading with Gapped Alignment and Empirical Pair Score Functions," J. Mol. Biol., 255, pp. 641-665, 1996.

Hellberg et al., "A Multivariate Approach to QSAR," Ph.D. Thesis, Umea, Sweden: University of Umea: 1986.

Nambier et al., "Total Synthesis and Cloning of a Gene Coding for the Ribonuclease S Protein," Science, 223: 1299-1301, 1984.

Lin et al., "Functional Expression of Horseradish Peroxidase in *E. coli* by Directed Evolution," Biotechnol. Prog, 15: 467-471, 1999.

Lathrop R.H., "The Protein Threading Problems with Sequence Amino Acids Interaction Preference is NP-Complete," Protein Eng., 7:1059-1068, 1994.

Hanes et al., "In Vitro Selection and Evolution of Functional Proteins by Using Ribosomes Display," Proc. Natl. Acad. Sci. USA, 94: 4937-4942, 1997.

Wells et al., "Rapid Evolution of Peptide and Protein Binding Properties in vitro," Curr Opin Biotechnol, 3:355-362, 1992.

Johnson et al., "The Traveling Salesman Problem: A Case Study in Local Optimization," in Local Search in Combinatorial Optimization, Edited by Aarts et al., John Wiley & Sons Ltd., 21-310, 1997.

Jonsson et al., "Quantitative Sequence-Activity Models (QSAM)—Tools for Sequence Design," Nucleic Acids Res., 21:733-739, 1993.

Geladi et al., "Partial Least Squares Regression: A Tutorial," Anal Chim Acta, 168: 1-17, 1986.

Holowachuk et al., "Efficient Gene Synthesis by Klenow Assembly/Extension-Pfu Polymerase Amplification (KAPPA) of Overlapping Olingonucleotides," PCR Methods Appl, 4:299-302, 1995.

Hellberg et al., "Minimum Analogue Peptide Sets (MAPS) for Quantitative Structure-Activity Relationships," Int J Pept Protein Res, 37:414-424, 1991.

Mee et al., "Design of Active Analogues of a D-Residue Peptide Using D-Optimal Design, QSAR and a Combinatorial Search Algorithm," J Pept Res, 49:89-102, 1997.

Schneider et al., "Peptide Design by Artificial Neural Networks and Compouter-Based Evolutionary Search," Proc Natl Acad Sci USA, 95:12179-12184, 1998.

Sjostrom et al.," Signal Peptide Amino Acid Sequences in *Escharichla coli* Contain Information Related to Final Protein Localization, A Multivariate Data Analysis," EMBO, 6:823-891, 1987.

Patel et al., "Patenting Computer-Designed Peptides," Journal of Computer-Aided Molecular Design, 12:543-556, 1998.

Aita et al., "Theory of Evolutionary Molecular Engineering Through Simultaneous Accumulation of Advantageous Mutations," J. Theor. Biol., 207:543-556, 2000.

Darius et al., "Simulated Molecular Evolution of Computer Generated Artifacts?," Biophysical Journal, 67:2120-2122, 1994.

Singh et al., "Application of Genetic Algorithms to Combinatorial Synthesis: A Computational Approach to Lead Identification and Lead Optimization," J.Am. Chem. Soc., 118:1669-1676, 1996.

Aita et al., "Analysis of Local Fitness Landscape with a Model of the Rough Mt. Fuji-Type Landscape: Application to Prolyl Endopeptidase and Thermolysin," Biopolymers. vol. 54, pp. 64-79, Accepted Jan. 14, 2000.

Gogos et al., "Assignment of Enzyme Substrate Specificity by Principal Component Analysis of Aligned Protein Sequences: An Experimental Test Using DNA Glycosylase Homologs," Proteins: Structure, Function, and Genetics, 40, pp. 98-105, 2000.

(56) References Cited

OTHER PUBLICATIONS

Vector NTI Suite 7.0 User's Manual (portion) describing software believed to be available prior to Feb. 1, 2000.
Tobin et al., "Directed Evolution: the 'Rational' Bases for 'Irrational' Design," Curr. Opin Struct Biol., 10:421-427, 2000.
van Regenmortel, M.H., "Are There Two Distinct Research Strategies for Developing Biologically Active Molecules: Rational Design and Empirical Selection?", J. Mol. Recognit, 13:1-4, 2000.
Ryu DD et all, "Recent Progress in Biomolecular Engineering," Biotechnol Prog., 16:2-16, 2000.
Gustafsson et al., "Exploration of Sequence Space for Protein Engineering," J. Mol. Recognit, 14:308-314, 2001.
Glieder et al., "Laboratory Evolution of a Soluble, Self-Sufficient, Highly Active Alkaline Hydroxylase," Nat Biotechnol, 20:1135-1139, 2002.
Lehman et al., "Exchanging the Active Site Between Phytases for Altering the Functional Properties of the Enzyme," Protein Sci, 9:1866-1872, 2000.
Kwasigroch et all, "PoPMuSiC, Rationally Designing Point Mutations in Protein Structures," Bioinformatics, 16:1701-1702, 2002.
Tangri et al., "Rationally Engineered Proteins or Antibodies with Absent or Reduced Immunogenicity," Curr Med Chem, 9:2191-2199, 2002.
Pierce et al., "Protein Design is NP-Hard," Protein Eng, 15:779-782, 2002.
Ness et al., "Molecular Breeding: The Natural Approach to Protein Design," Adv Protein Chem, 55:261-292, 2000.
Lehmann et al., "The Consensus Concept for Thermostability Engineering of Proteins: Further Proof of Concept," Protein Eng., 15:403-411, 2002.
Dimmic et al., "rtREV: An Amino Acid Substitution Matrix for Inference of Retrovirus and Reverse Transcriptase Phylogeny," J. Mol Evol, 55:65-73, 2002.
Aita et al., "A Cross-Section of the Fitness Landscape of Dihydrofolate Reductase," Protein Eng, 14:633-638, 2001.
Strom et al., "Important Structural Features of 15-Residue Lactoferricin Derivatives and Methods for Improvement of Antimicrobial Activity," Biochem Cell Biol, 80:65-74, 2002.
Choulier et al., "QSAR Studies Applied to the Prediction of Antigen-Antibody Interaction Kinetics as Measured by BIACORE," Protein Eng, 15(5):378-382, (2002).
Hoover et al., "DNAWorks: an Automated Method for Designing Oligonucleotides for PCR-Based Gene Synthesis," Nucleic Acids Res, 30:E43, 2002.
Abecassis et all, "High Efficiency Family Shuffling Based on Multi-Step PCR and In vivo DNA Recombination in Yeast: Statistical and Functional Analysis of a Combinatorial Library Between Human Cytochrome P460 1A1 and 1A2," Nucleic Acids Res., 28:E88, 2000.
Aita et al., "Surveying a Local Fitness Landscape of a Protein with Epistatic Altee for the Study of Directed Evolution," Biopolymers, 64:95-106, 2002.
Prusis et al., "Proteo-chemometrics Analysis of MSH Peptide Binding to Melancortin Receptors," Protein Eng, 15:305-311, 2002.
Prusis et al., "PLS Modeling of Chimeric MS04/MSH-Peptide and MC1/MC3-Receptor Interaction Reveals a Novel Method for the Analysis of Ligand-Receptor Interactions," Biochim Biophys Acta, 1544(1-2):350-357, 2001.
Lu et al., "Predicting the Reactivity of Proteins from Their Sequence Alone: Kazal Family of Protein Inhibitors of Serine Proteinases," Proc Natl Acad Sci USA, 98(4):1410-1415, 2001.
Schein et al., "Chloroplast Transit Peptide Prediction: A Peek Inside the Black Box," Nucleic Acids Res, 29:E82, 2001.
Fariselli et al., "Prediction of Protein-Protein Interaction Sites in Heterocomplexes with Neural Networks," Eur J Biochem, 269:1356-1361, 2002.
Fariselli et al., "Prediction of Contact Maps with Neural Networks and Correlated Mutations," Protein Eng, 14(11): 835-843, 2001.
Marvanova et al., "Biochemical Characterization of Broad-Specificity Enzymes Using Multivariate Experimental Design and a Colorimetric Microplate Assay: Characterization of the Haloalkane Dehalogenase Mutants," J. Microbiol Methods, 44:14-157, 2001.
Looger et al., Computational Design of Receptor and Sensor Proteins with Novel Functions, Nature, 423:185-190, 2003.
Govindarajan et al., "Systematic Variation of Amino Acid Substitutions for Stringent Assessment of Pairwise Covariation," J. Mol. Biol, 328:1061-1069, 2003.
del Sol Mesa et al., "Automatic Methods for Predicting Functionality Important Residues," J Mol Biol, 326:1289-1302, 2003.
Benos et al., "Additivity in Protein-DNA Interactions: How Good an Approximation is it?" Nucleic Acids Res 30(20): 4442-51, 2002.
Bogarad et al., "A Hierarchical Approach to Protein Molecular Evolution," Proc Natl Acad Sci USA, 96:2591-2595, 0666, (1999).
Carlsen et al., "QSAR's Based on Partial Order Ranking," SAR QSAR Environ Res, 13(1): 153-165, 2002.
Crameri et al., "DNA Shuffling of a Family of Genes from Diverse Species Accelerates Directed Evolution," Nature, 391:288-291, 1998.
Dill K.A., "Additivity Principles in Biochemistry," J Biol Chem, 272(2): 701-704, 1997.
Distefano et al., "Quantifying Beta-Sheet Stability by Phage Display," J Mol Biol, 322(1):179-188, 2002.
Hayes et al., "Combining Computational and Experimental Screening for Rapid Optimization of Protein Properties," Proc Natl Acad Sci USA, 99(25):15926-15931, 2002.
Kell, D.B., "Metabolomics and Machine Learning: Explanatory Analysis of Complex Metabolome Data Using Genetic Programming to Produce Simple, Robust Rules," Mol Biol Rep, 29(1-2): 237-241, 2002.
Koshi et al., "Context-Dependent Optimal Substitution Matrices," Protein Eng, 8:641-645, 1995.
Koshi et al., "Mutation Matrices and Physical-Chemical Properties: Correlations and Implications," Proteins 27(3):336-344, 1997.
Lahr et al., "Patterned Library Analysis: A Method for the Quantitative Assessement of Hypotheses Concerning the Determinants of Protein Structure," Proc Natl Acad Sci USA, 96(26):14860-14865, 1999.
Lapinsh et al., "Classification of G-Protein Coupled Receptors by Alignment Independent Extraction of Principal Chemical Properties of Primary Amino Acid Sequences," Protein Sci 11(4):795-805, (2002).
Lapinsh et al., "Development of Proteo-Chemometrics: A Novel Technology for the Analysis of Drug-Receptor Interactions," Biochim Biophys Acata, 1525(1-2): 180-190, (2001).
Lapinsh et al., "Protechemometrics Modeling of the Interaction of Amine G-Protein Coupled Receptors with a Diverse Set of Ligands," Mol Pharmacol 61(6): 1465-1475, 2002.
Lapinsh et al., "QSAR and Proteo-Chemometric Analysis of the Interaction of a Series of Organic Compounds with Melanocortin Receptor Subtypes," J Med Chem, 46(13): 2572-2579, 2003.
Lee et al., "Mathematical Modelling of Inset Neuropeptide Potencies. Are Quantitatively Predictive Models Possible," Insect Biochem Mol Biol, 30(10): 899-907, 2000.
Lehman et al., "Engineering Proteins Thermostability: the Use of sequence Alignments Versus Rational Design and Directed Evolution," Current Opinion in Biotechnology 12:371-375, 2001.
Linusson et al., Statistical Molecular Design of Building Blocks for Combinatorial Chemistry, J Med Chem, 43(7): 1320-1328, 2000.
Matsuura eta l., "Nonaddivity of Mutational Effects on the Properties of Catalasa I and its Application to Efficient Directed Evolution," Protein Eng, 11(9): 789-795, 1998.
Nakai et al., "Structure Modification and Functionality of Why Proteins: Quantitative Structure-Activity Relationship Approach," J Dairy Sci, 68(10):2763-2772, 1985.
Nakai et al., "Recent Advances in Structure and Function of Food Proteins: QSAR Approach," Crit Rev Food Sci Nutr, 33(6):477-499, (1993).
Ness et al., "Synthetic Shuffling Expands Functional Protein Diversity by Allowing Amino Acids to Recombine Independently," Nat Biotechnol, 20(12):1251-1255, 2002.
Niggemann et al., "Exploring Local and Non-Local Interactions for Protein Stability by Structural Motif Engineering," J Mol Biol, 296(1):181-195, 2000.

(56) References Cited

OTHER PUBLICATIONS

Nikolova et al., "Semirational Design of Active Tumor Suppressor p53 DNA Binding Domain with Enhanced Stability," Proc Natl Acad Sci USA, 95(25): 14675-14680, 1998.
Reymond et al., "Substrate Arrays as Enzyme Fingerprinting Tools," Chembiochem, 3(8):701-708, 2002.
Sadowski et al., "Automated Generation and Refinement of Protein Signatures: Case Study with G-Protein Coupled Receptors," Bioinformatics, 19(6(: 727-734, 2003.
Shaw et al., "Predicting Amino Acid Residues Responsible for Enzyme Specificity Solely from Protein Sequences," Biotechnol Bioeng, 79(3): 295-300, 2002.
Sheridan et al., "Designing Targeted Libraries with Genetic Algorithms," J Mol Graph Model, 18(4-5): 320-345, 525, 2000.
Siebert, K.J., "Quantitative Structure-Activity Relationship Modeling of Peptide and Protein Behavior as a Function of Amino Acid Composition," J Agric Food Chem, 49(2): 851-858, 2001.
Siebert, K.J., "Modeling Protein Function Properties from Amino Acid Composition," J Agric Food Chem, 51(26): 7792-7797, 2003.
Soyer et al., "Using Evolutionary Methods to Study G-Protein Coupled Receptors," Pac Symp Biocomput: 625-636, 2002.
Steipe, B., "Evolutionary Approaches to Protein Engineering," Curr Top Microbiol Immunol, 243: 55-86, 1999.
Umeno et al., "Evolution of the C30 Carotenoid Synthase CrtM for Function in a C40 Pathway," J Bacteriol 184(23): 6690-6699, 2002.
Veraverbeke et al., "Wheat Protein Composition and Properties of Wheat Glutenin in Relation to Breadmaking Functionality," Crit Rev Food Sci Nutr, 42(3): 179-208, 2002.
Wahler et al., "Enzyme Fingerprints by Fluorogenic and Chromogenic Substrate Arrays," Angew Chem Int Ed Engl,, 40(23): 4457-4460, 2001.
Wahler et al., "Enzyme Fingerprints of Activity, and Stereo and Enantioselectivity from Fluorogenic and Chromogenic Substrate Arrays," Chemistry, 8(14): 3211-3228, 2002.
Wang et al., "Designing Gene Libraries from Protein Profiles for Combinatorial Protein Experiments," Nucleic Acids Res, 30(21): e120, 2002.
Wells, J.A., "Additivity of Mutational Effects in Proteins," Biochemistry, 29(37): 8509-8517, 1990.
Wikberg et al., "Melanocortin Receptors: Ligands and Protechemometrics Modeling," Ann NY Acad Sci, 994:21-26, 2003.
Martin et al., "Measuring Diversity: Experimental Design of Combinatorial Libraries for Drug Discovery," J. Med. Chem. 38, 1431-1436, 1995.
Sheridan et al., "Using a Genetic Algorithm to Suggest Combinatorial Libraries," J. Chem. Inf. Compu. Sci., 35, 310-320, 1995.
D.K. Agrafiotis, "Multiobjective Optimization of Combinatorial Libraries," IBM J. Res & Dev., Vol, 45, No. 3, 545-566, 2001.
Ness et al., "Synthetic Shuffling Expands Functional Protein Diversity by Allowing Amino Acids to Recombine Independently," Nature Biotechnology, vol. 20, 1251-1255 (2002).
Kolkman et al., "Directed Evolution of Proteins by Exon Shuffling," Nature Biotechnology, vol. 19, 423-428 (2001).
Voigt et al., "Computationally Focusing the Directed Evolution of Proteins," Journal of Cellular Biochemistry Supplement 37:58-63 (2001).
U.S. Appl. No. 13/095,767, filed Apr. 27, 2011, Selifonov et al.
U.S. Appl. No. 13/168,654, filed Jun. 24, 2011, Gustafsson et al.
US Office Action dated Apr. 18, 2007 issued in U.S. Appl. No. 10/379,378.
US Office Action dated Feb. 21, 2008 issued in U.S. Appl. No. 10/379,378.
US Final Office Action dated Sep. 17, 2008 issued in U.S. Appl. No. 10/379,378.
US Final Office Action (Supplementary) dated Oct. 15, 2008 issued in U.S. Appl. No. 10/379,378.
US Office Action (Advisory Action) dated Mar. 2, 2009 issued in U.S. Appl. No. 10/379,378.
US Office Action dated Jun. 12, 2009 issued in U.S. Appl. No. 10/379,378.
US Office Action (Examiner Interview Summary) dated Mar. 11, 2010 issued in U.S. Appl. No. 10/379,378.
US Notice of Allowance dated Mar. 29, 2010 issued in U.S. Appl. No. 10/379,378.
US Office Action (Miscellaneous Communication) dated May 25, 2010 issued in U.S. Appl. No. 10/379,378.
US Office Communication (Response to Rule 312 Communication) dated May 27, 2010 issued in U.S. Appl. No. 10/379,378.
US Office Action dated Jun. 15, 2006 issued in U.S. Appl. No. 10/629,351.
US Office Action dated Nov. 29, 2006 issued in U.S. Appl. No. 10/629,351.
US Office Action dated Sep. 18, 2007 issued in U.S. Appl. No. 10/629,351.
US Final Office Action dated Dec. 11, 2008 issued in U.S. Appl. No. 10/629,351.
US Office Action dated Jun. 9, 2009 issued in U.S. Appl. No. 10/629,351.
US Notice of Allowance dated Mar. 24, 2010 issued in U.S. Appl. No. 10/629,351.
US Office Action (Miscellaneous Communication) dated Apr. 8, 2010 issued in issued in U.S. Appl. No. 10/629,351.
US Office Action dated May 27, 2009 issued in U.S. Appl. No. 11/981,577.
US Notice of Allowance dated Mar. 9, 2010 issued in U.S. Appl. No. 11/981,577.
US Office Communication (Response to Rule 312 Communication) dated Jun. 1, 2010 issued in U.S. Appl. No. 11/981,577.
US Office Action dated Apr. 2, 2010 issued in U.S. Appl. No. 11/429,628.
US Examiner Interview Summary dated Sep. 17, 2010 issued in U.S. Appl. No. 11/429,628.
US Office Action Final dated Jan. 14, 2011 issued in U.S. Appl. No. 11/429,628.
US Office Action dated Mar. 13, 2007 issued in U.S. Appl. No. 10/874,802.
US Office Action dated Jun. 10, 2009 issued in U.S. Appl. No. 11/706,034.
US Notice of Allowance dated Mar. 9, 2010 issued in U.S. Appl. No. 11/706,034.
US Office Action (Miscellaneous Communication) dated Apr. 8, 2010 issued in U.S. Appl. No. 11/706,034.
US Office Action dated Jun. 14, 2010 issued in U.S. Appl. No. 12/557,465.
US Office Action dated Jun. 14, 2010 issued in U.S. Appl. No. 12/557,467.
US Office Action dated Jun. 15, 2010 issued in U.S. Appl. No. 12/557,469.
US Office Action dated May 29, 2009 issued in U.S. Appl. No. 11/981,567.
US Examiner Interview Summary dated Mar. 11, 2010 issued in U.S. Appl. No. 11/981,567.
US Office Action Final dated Mar. 19, 2010 issued in U.S. Appl. No. 11/981,567.
US Examiner Interview Summary dated Sep. 17, 2010 issued in U.S. Appl. No. 11/981,567.
US Office Action dated Aug. 30, 2010 issued in U.S. Appl. No. 11/981,566.
US Preliminary Amendment dated Apr. 27, 2011 filed in U.S. Appl. No. 13/095,797.
PCT International Search Report dated Oct. 27, 2003 issued in PCT/US03/06551.
PCT International Preliminary Examination Report dated Jun. 25, 2007 issued in PCT/US03/06551.
European Search Report (Supplemental) dated Feb. 13, 2006 issued in EP 03 743 748.0-2201.
European Examination Report dated Jul. 31, 2008 issued in EP 03 743 748.0-2405.
European Communication dated Jan. 13, 2010 issued in EP 03 743 748.0-2405.
JP Office Action dated Feb. 26, 2009 issued in JP 2003-573522.
JP Final Office Action dated Feb. 24, 2010 issued in JP 2003-573522.

(56) References Cited

OTHER PUBLICATIONS

PCT International Search Report dated Nov. 24, 2005 issued in PCT/US2005/022119.
PCT International Preliminary Report on Patentability and Written Opinion dated Dec. 28, 2006 issued in PCT/US2005/022119.
European Examination Report dated Dec. 23, 2008 issued in EP 05 779 687.2-2405.
European Examination Report dated Jun. 7, 2010 issued in EP 05 779 687.2-2405.
Japanese Office Action dated Jan. 21, 2011 issued in JP 2007-518248.
Agrafiotis, et al. (2002) "On the Use of Neural Network Ensembles in QSAR and QSPR", *J. Chem Inf. Computer Science*, 42:903-911.
Atchley et al., (2000) "Correlations Among Amino Acid Sites in bHLH Protein Domains: An Information Theoretic Analysis", *Mol. Biol. Evol.* 17(1):164-178.
Cho et al., (1998) "Rational Combinatorial Library Design. 2. Rational Design of Targeted Combinatorial Peptide Libraries Using Chemical Similarity Probe and the Inverse QSAR Approaches," *J. Chem. Inf. Comput. Sci.* 38(2):259-268.
Dahiyat et al., (1996) "Protein Design Automation," *Protein Science* 5:895-903.
Fox, Richard (2005) "Directed Molecular Evolution by Machine Learning and the Influence of Nonlinear Interactions," *Journal of Theoretical Biology* 234:187-199.
Ginalski et al., (2005) "Practical Lessons From Protein Structure Prediction," *Nucleic Acids Research*, 33( 6):1874-1891.
Gribskov, et al. (Jul. 1987) "Profile analysis: Detection of distantly related proteins" Proc. Natl. Acad. Sci. USA, *Biochemistry* 84:4355-4358.
Hellberg et al., (1987) "Peptide Quantitative Structure-Activity Relationships, a Multivariate Approach," *Journal of Medicinal Chemistry*, 30:1126-1135.
Hu et al., (2004) "Developing Optimal Non-Linear Scoring Function for Protein Design," *Bioinformatics*, 20(17):3080-3098.
Krogh, Anders (1998) "An Introduction to Hidden Markov Models for Biological Sequences," *Computational Methods in Molecular Biology*, edited by S.L. Salzberg, D.B. Searls and S. Kasif, pp. 45-63.
Moore et al., (Feb. 2004) "Computational Challenges in Combinatorial Library Design in Protein Engineering," *AIChE Journal*, 50(2):262-272.
Perelson et al., (1995) "Protein evolution on partially correlated landscapes", *PNAS* USA 92:9657-9661.
Zhang et al., (Feb. 2002) "Genome Shuffling Leads to Rapid Phenotypic Improvement in Bacteria," *Nature*, 415:644-646.

US Office Action dated Nov. 10, 2011 issued in U.S. Appl. No. 11/981,567.
European Examination Report dated Oct. 4, 2011 issued in EP 03 743 748.0-2405.
Japanese Office Action dated Sep. 1, 2011 issued in JP 2003-573522.
European Examination Report dated Dec. 8, 2011 issued in EP 05 779 687.2-2405.
Japanese Notice of Final Rejection dated Feb. 8, 2012 issued in JP 2007518248.
US Office Action dated Mar. 29, 2012 issued in U.S. Appl. No. 11/429,628.
US Office Action Final dated Jan. 3, 2013 issued in U.S. Appl. No. 11/429,628.
US Office Action dated Sep. 13, 2013 issued in U.S. Appl. No. 11/429,628.
US Office Action dated Mar. 30, 2012 issued in U.S. Appl. No. 13/168,654.
US Office Action (Letter Restarting Period for Response) dated Apr. 17, 2012 issued in U.S. Appl. No. 13/168,654.
US Office Action Final dated Feb. 22, 2013 issued in U.S. Appl. No. 13/168,654.
US Advisory Action Before the Filing of an Appeal Brief dated Sep. 12, 2013 issued in U.S. Appl. No. 13/168,654.
US Office Action Final dated Aug. 14, 2012 issued in U.S. Appl. No. 11/981,567.
US Office Action dated Jul. 3, 2012 issued in U.S. Appl. No. 13/095,797.
US Office Action Final dated Apr. 11, 2013 issued in U.S. Appl. No. 13/095,797.
US Advisory Action Before the Filing of an Appeal Brief dated Jul. 16, 2013 issued in U.S. Appl. No. 13/095,797.
European Search Report (Supplemental Partial) dated Nov. 28, 2005 issued in EP 03 743 748.0-2201.
European Communication dated Jan. 18, 2013 issued in EP 03 743 748.0-2405.
European Communication (Result of consultation) dated Mar. 19, 2013 issued in EP 03 743 748.0-2405.
European Communication (Result of consultation) dated Jul. 4, 2013 issued in EP 03 743 748.0-1410.
JP Office Action (Notice of Reasons for Rejection) dated Jun. 21, 2012 issued in JP 2003-573522.
JP Office Action dated Apr. 10, 2012 issued in JP 2009-123638.
Wold et al. (2001) "PLS-regression: a basic tool of chemometrics," *Chemometrics and Intelligent Laboratory Systems*, 58:109-130.
European Communication dated Jan. 23, 2014 issued in EP 03 743 748.0-1410.

\* cited by examiner

METHODS, SYSTEMS, AND SOFTWARE FOR IDENTIFYING FUNCTIONAL BIOMOLECULES

CROSS-REFERENCE TO RELATED APPLICATIONS

This application is a continuation of U.S. patent application Ser. No. 10/874,802, filed Jun. 22, 2004, now abandoned naming Richard John Fox as inventor, which is a continuation-in-part of U.S. patent application Ser. No. 10/629,351, filed Jul. 29, 2003, now U.S Pat. No. 7,747,391 naming Richard John Fox as inventor, which is a continuation-in-part of U.S. patent application Ser. No. 10/379,378, filed Mar. 3, 2003, now U.S Pat. No. 7,783,428 naming Gustaffson et al. as inventors which in turn claims priority under 35 USC 119(e) from U.S. Provisional Application No. 60/360,982, filed Mar. 1, 2002. Each of these documents is incorporated herein by reference in its entirety and for all purposes.

BACKGROUND

The present invention relates to the fields of molecular biology, molecular evolution, bioinformatics, and digital systems. More specifically, the invention relates to methods for computationally predicting the activity of a biomolecule. Systems, including digital systems, and system software for performing these methods are also provided. Methods of the present invention have utility in the optimization of proteins for industrial and therapeutic use.

Protein design has long been known to be a difficult task if for no other reason than the combinatorial explosion of possible molecules that constitute searchable sequence space. The sequence space of proteins is immense and is impossible to explore exhaustively. Because of this complexity, many approximate methods have been used to design better proteins; chief among them is the method of directed evolution. Directed evolution of proteins is today dominated by various high throughput screening and recombination formats, often performed iteratively.

In parallel, various computational techniques have been proposed for exploring sequence-activity space. Relatively speaking, these techniques are in their infancy and significant advances are still needed. Accordingly, new ways to efficiently search sequence space to identify functional proteins would be highly desirable.

SUMMARY

The present invention provides techniques for generating and using models that employ non-linear terms, particularly terms that account for interactions between two or more residues in the sequence. These non-linear terms may be "cross product" terms that involve multiplication of two or more variables, each representing the presence (or absence) of the residues participating in the interaction. In some embodiments, the invention involves techniques for selecting the non-linear terms that best describe the activity of the sequence. Note that there are often far more possible non-linear interaction terms than there are true interactions between residues. Hence, to avoid overfitting, only a limited number of non-linear are typically employed and those employed should reflect interactions that affect activity.

One aspect of the invention provides a method for identifying amino acid residues for variation in a protein variant library. This method may be characterized by the following operations: (a) receiving data characterizing a training set of a protein variant library, (b) from the data, developing a sequence-activity model that predicts activity as a function of amino acid residue type and corresponding position in a protein sequence; and (c) using the sequence-activity model to identify one or more amino acid residues at specific positions for variation to impact the desired activity. The sequence-activity model includes one or more non-linear terms, each of which represents an interaction between two or more amino acid residues in the protein sequence. The training set data provides activity and sequence information for each protein variant in the training set.

The protein variant library may include proteins from various sources. In one example, the members include naturally occurring proteins such as those encoded by members of a single gene family. In another example, the members include proteins obtained by using a recombination-based diversity generation mechanism. For example, DNA fragmentation-mediated recombination, synthetic oligonucleotide-mediated recombination or a combination thereof may be performed on nucleic acids encoding all or part of one or more naturally occurring parent proteins for this purpose. In still another example, the members are obtained by performing DOE to identify the systematically varied sequences.

In some embodiments, at least one non-linear term is a cross-product term containing a product of one variable representing the presence of one interacting residue and another variable representing the presence of another interacting residue. The form of the sequence-activity model may be a sum of at least one cross-product term and one or more linear terms, with each of the linear terms representing the presence of a variable residue in the training set. The cross-product terms may be selected from a group of potential cross-product terms by various techniques including, for example, running a genetic algorithm to select the cross-product terms based upon the predictive ability of various models employing different cross-product terms.

The sequence activity model may be produced from the training set by many different techniques. In a preferred embodiment, the model is a regression model such as a partial least squares model or a principal component regression model. In another example, the model is a neural network.

In some embodiments, the method also includes (d) using the sequence activity model to identify one or more amino acid residues that are to remain fixed (as opposed to being varied) in new protein variant library.

Using the sequence activity model to identify residues for fixing or variation may involve any of many different possible analytical techniques. In some cases, a "reference sequence" is used to define the variations. Such sequence may be one predicted by the model to have a highest value (or one of the highest values) of the desired activity. In another case, the reference sequence may be that of a member of the original protein variant library. From the reference sequence, the method may select subsequences for effecting the variations. In addition or alternatively, the sequence activity model ranks residue positions (or specific residues at certain positions) in order of impact on the desired activity.

One goal of the method may be to generate a new protein variant library. As part of this process, the method may identify sequences that are to be used for generating this new library. Such sequences include variations on the residues identified in (c) above or are precursors used to subsequently introduce such variations. The sequences may be modified by performing mutagenesis or a recombination-based diversity generation mechanism to generate the new library of protein variants. This may form part of a directed evolution procedure. The new library may also be used in developing a new sequence activity model. The new protein variant library is analyzed to assess effects on a particular activity such as stability, catalytic activity, therapeutic activity, resistance to a pathogen or toxin, toxicity, etc.

In some embodiments, the method involves selecting one or more members of the new protein variant library for production. One or more of these may then be synthesized and/or expressed in an expression system. In a specific embodiment, the method continues in the following manner: (i) providing an expression system from which a selected member of the new protein variant library can be expressed; and (ii) expressing the selected member of the new protein variant library.

In some embodiments, rather than use amino acid sequences, the methods employ nucleotide sequences to generate the models and predict activity. Variations in groups of nucleotides, e.g., codons, affect the activity of peptides encoded by the nucleotide sequences. In some embodiments, the model may provide a bias for codons that are preferentially expressed (compared to other codons encoding the same amino acid) depending upon the host employed to express the peptide.

Yet another aspect of the invention pertains to apparatus and computer program products including machine-readable media on which are provided program instructions and/or arrangements of data for implementing the methods and software systems described above. Frequently, the program instructions are provided as code for performing certain method operations. Data, if employed to implement features of this invention, may be provided as data structures, database tables, data objects, or other appropriate arrangements of specified information. Any of the methods or systems of this invention may be represented, in whole or in part, as such program instructions and/or data provided on machine-readable media.

These and other features of the present invention will be described in more detail below in the detailed description of the invention and in conjunction with the following figures.

DETAILED DISCUSSION OF THE INVENTION

I. Definitions

Figure 1:
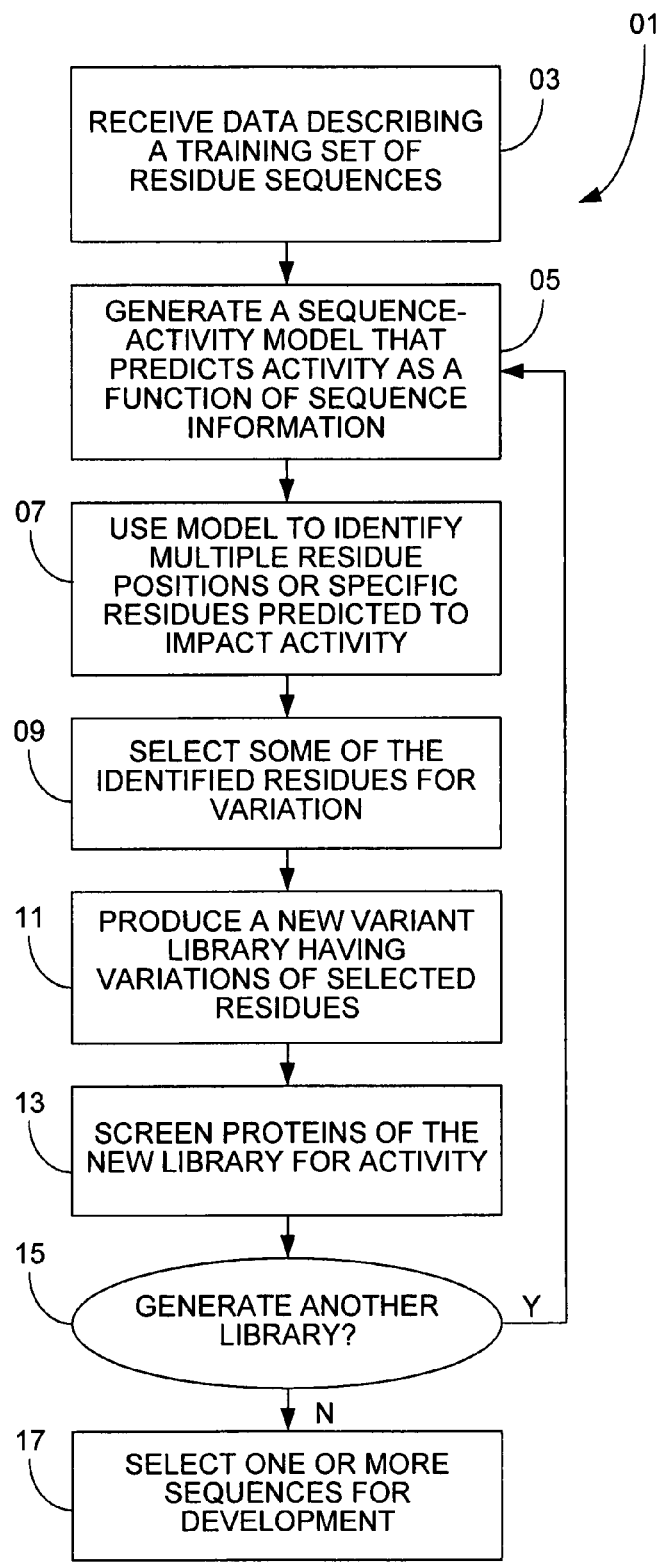
FIG. 1 is a flow chart depicting a sequence of operations, including identifying particular residues for variation, that may be used to generate one or more generations of protein variant libraries.

Before describing the present invention in detail, it is to be understood that this invention is not limited to particular sequences, compositions, algorithms, or systems, which can, of course vary. It is also to be understood that the terminology used herein is for the purpose of describing particular embodiments only, and is not intended to be limiting. As used in this specification and appended claims, the singular forms "a", "an", and "the" include plural referents unless the content and context clearly dictates otherwise. Thus, for example, reference to "a device" includes a combination of two or more such devices, and the like. Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected).

The following definitions and those included throughout this disclosure supplement those known to persons of skill in the art.

A "bio-molecule" refers to a molecule that is generally found in a biological organism. Preferred biological molecules include biological macromolecules that are typically polymeric in nature being composed of multiple subunits (i.e., "biopolymers"). Typical bio-molecules include, but are not limited to, molecules that share some structural features with naturally occurring polymers such as RNAs (formed from nucleotide subunits), DNAs (formed from nucleotide subunits), and polypeptides (formed from amino acid subunits), including, e.g., RNAs, RNA analogues, DNAs, DNA analogues, polypeptides, polypeptide analogues, peptide nucleic acids (PNAs), combinations of RNA and DNA (e.g., chimeraplasts), or the like. Bio-molecules also include, e.g., lipids, carbohydrates, or other organic molecules that are made by one or more genetically encodable molecules (e.g., one or more enzymes or enzyme pathways) or the like.

The term "nucleic acid" refers to deoxyribonucleotides or ribonucleotides and polymers (e.g., oligonucleotides, polynucleotides, etc.) thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with, e.g., oligonucleotide, polynucleotide, cDNA, and mRNA.

A "nucleic acid sequence" refers to the order and identity of the nucleotides comprising a nucleic acid.

A "polynucleotide" is a polymer of nucleotides (A, C, T, U, G, etc. or naturally occurring or artificial nucleotide analogues) or a character string representing a polymer of nucleotides, depending on context. Either the given nucleic acid or the complementary nucleic acid can be determined from any specified polynucleotide sequence.

The terms "polypeptide" and "protein" are used interchangeably herein to refer to a polymer of amino acid residues. Typically, the polymer has at least about 30 amino acid residues, and usually at least about 50 amino acid residues. More typically, they contain at least about 100 amino acid residues. The terms apply to amino acid polymers in which one or more amino acid residues are analogs, derivatives or mimetics of corresponding naturally occurring amino acids, as well as to naturally occurring amino acid polymers. For example, polypeptides can be modified or derivatized, e.g., by the addition of carbohydrate residues to form glycoproteins.

The terms "polypeptide," and "protein" include glycoproteins, as well as non-glycoproteins.

A "motif" refers to a pattern of subunits in or among biological molecules. For example, the motif can refer to a subunit pattern of the unencoded biological molecule or to a subunit pattern of an encoded representation of a biological molecule.

"Screening" refers to the process in which one or more properties of one or more bio-molecule is determined. For example, typical screening processes include those in which one or more properties of one or more members of one or more libraries is/are determined.

The term "covariation" refers to the correlated variation of two or more variables (e.g., amino acids in a polypeptide, etc.).

"Directed evolution" or "artificial evolution" refers to a process of artificially changing a character string by artificial selection, recombination, or other manipulation, i.e., which occurs in a reproductive population in which there are (1) varieties of individuals, with some varieties being (2) heritable, of which some varieties (3) differ in fitness (reproductive success determined by outcome of selection for a predetermined property (desired characteristic). The reproductive population can be, e.g., a physical population or a virtual population in a computer system.

A "data structure" refers to the organization and optionally associated device for the storage of information, typically multiple "pieces" of information. The data structure can be a simple recordation of the information (e.g., a list) or the data structure can contain additional information (e.g., annotations) regarding the information contained therein, can establish relationships between the various "members" (i.e., information "pieces") of the data structure, and can provide pointers or links to resources external to the data structure. The data structure can be intangible but is rendered tangible when stored or represented in a tangible medium (e.g., paper, computer readable medium, etc.). The data structure can represent various information architectures including, but not limited to simple lists, linked lists, indexed lists, data tables, indexes, hash indices, flat file databases, relational databases, local databases, distributed databases, thin client databases, and the like. In preferred embodiments, the data structure provides fields sufficient for the storage of one or more character strings. The data structure is optionally organized to permit alignment of the character strings and, optionally, to store information regarding the alignment and/or string similarities and/or string differences. In one embodiment, this information is in the form of alignment "scores" (e.g., similarity indices) and/or alignment maps showing individual subunit (e.g., nucleotide in the case of nucleic acid) alignments. The term "encoded character string" refers to a representation of a biological molecule that preserves desired sequence/structural information regarding that molecule. As noted throughout, non-sequence properties of bio-molecules can be stored in a data structure and alignments of such non-sequence properties, in a manner analogous to sequence based alignment can be practiced.

A "library" or "population" refers to a collection of at least two different molecules, character strings, and/or models, such as nucleic acid sequences (e.g., genes, oligonucleotides, etc.) or expression products (e.g., enzymes) therefrom. A library or population generally includes a number of different molecules. For example, a library or population typically includes at least about 10 different molecules. Large libraries typically include at least about 100 different molecules, more typically at least about 1000 different molecules. For some applications, the library includes at least about 10000 or more different molecules.

"Systematic variance" refers to different descriptors of an item or set of items being changed in different combinations.

"Systematically varied data" refers to data produced, derived, or resulting from different descriptors of an item or set of items being changed in different combinations. Many different descriptors can be changed at the same time, but in different combinations. For example, activity data gathered from polypeptides in which combinations of amino acids have been changed is systematically varied data.

The terms "sequence" and "character strings" are used interchangeably herein to refer to the order and identity of amino acid residues in a protein (i.e., a protein sequence or protein character string) or to the order and identity of nucleotides in a nucleic acid (i.e., a nucleic acid sequence or nucleic acid character string).

II. Generating Improved Protein Variant Libraries

In accordance with the present invention, various methods are provided for generating new protein variant libraries that can be used to explore protein sequence and activity space. A feature of many such methods is a procedure for identifying amino acid residues in a protein sequence that are predicted to impact a desired activity. As one example, such procedure includes the following operations:

(a) receiving data characterizing a training set of protein variants, wherein the data provides activity and sequence information for each protein variant in the training set;

(b) from the data, developing a sequence activity model that predicts activity as a function of amino acid residue type and corresponding position in the sequence (preferably the model includes one or more non-linear terms, each representing an interaction between two or more amino acid residues); and (c) using the sequence activity model to identify one or more amino acid residues at specific positions in one or more protein variants that are to be varied in order to impact the desired activity.

FIG. 1 presents a flow chart showing one application of the present invention. It presents various operations that may be performed in the order depicted or in some other order. As shown, a process 01 begins at a block 03 with receipt of data describing a training set comprising residue sequences for a protein variant library. In other words, the training set data is derived from a protein variant library. Typically that data will include, for each protein in the library, a complete or partial residue sequence together with an activity value. In some cases, multiple types of activities (e.g., rate constant data and thermal stability data) are provided together in the training set.

In many embodiments, the individual members of the protein variant library represent a wide range of sequences and activities. This allows one to generate a sequence-activity model having applicability over a broad region of sequence space. Techniques for generating such diverse libraries include systematic variation of protein sequences and directed evolution techniques. Both of these are described in more detail elsewhere herein. Note however that it is often desirable to generate models from gene sequences representing a particular gene family; e.g., a particular kinase found in multiple species. As most residues will be identical across all members of the family, the model describes only those residues that vary. Thus statistical models based on such relatively small training sets, compared to the set of all possible variants, are valid in a local sense. The goal is not to find a global fitness function since that is beyond the capacity (and often the need) of the systems under consideration.

Activity data may be obtained by assays or screens appropriately designed to measure activity magnitudes. Such techniques are well known and are not central to this invention. The principles for designing appropriate assays or screens are widely understood. Techniques for obtaining protein sequences are also well known and are not central to this invention. The activity used with this invention may be protein stability (e.g., thermal stability). However, many important embodiments consider other activities such as catalytic activity, resistance to pathogens and/or toxins, therapeutic activity, toxicity, and the like.

After the training set data has been generated or acquired, the process uses it to generate a sequence-activity model that predicts activity as a function of sequence information. See block 05. Such model is a non-linear expression, algorithm or other tool that predicts the relative activity of a particular protein when provided with sequence information for that protein. In other words, protein sequence information is input and an activity prediction is output. For many embodiments of this invention, the model can also rank the contribution of various residues to activity. Methods of generating such models, which all fall under the rubric of machine learning, (e.g., partial least squares regression (PLS), principal component regression (PCR), and multiple linear regression (MLR)) will be discussed below, along with the format of the independent variables (sequence information), the format of the dependent variable(s) (activity), and the form of the model itself (e.g., a linear first order expression).

A model generated at block 05 is employed to identify multiple residue positions (e.g., position 35) or specific residue values (e.g. glutamine at position 35) that are predicted to impact activity. See block 07. In addition to identifying such positions, it may "rank" the residue positions or residue values based on their contributions to activity. For example, the model may predict that glutamine at position 35 has the most pronounced, positive effect on activity, phenylalanine at position 208 has the second most pronounced, positive effect, and so on. In a specific approach described below, PLS or PCR regression coefficients are employed to rank the importance of specific residues. In another specific approach, a PLS load matrix is employed to rank the importance of specific residue positions.

After the process has identified residues that impact activity, some of them are selected for variation as indicated at a block 09. This is done for the purpose of exploring sequence space. Residues are selected using any of a number of different selection protocols, some of which will be described below. In one example, specific residues predicted to have the most beneficial impact on activity are preserved (i.e., not varied). A certain number of other residues predicted to have a lesser impact are, however, selected for variation. In another example, the residue positions found to have the biggest impact on activity are selected for variation, but only if they are found to vary in high performing members of the training set. For example, if the model predicts that residue position 197 has the biggest impact on activity, but all or most of the proteins with high activity have leucine at this position, then position 197 would not be selected for variation in this approach. In other words, all or most proteins in a next generation library would have leucine at position 197. However, if some "good" proteins had valine at this position and others had leucine, then the process would choose to vary the amino acid at this position. In some cases, it will be found that a combination of two or more interacting residues have the biggest impact on activity. Hence, in some strategies, these residues are co-varied.

After the residues for variation have been identified, the method next generates a new variant library having the specified residue variation. See block 11. Various methodologies are available for this purpose. In one example, an in vitro or in vivo recombination-based diversity generation mechanism is performed to generate the new variant library. Such procedures may employ oligonucleotides containing sequences or subsequences for encoding the proteins of the parental variant library. Some of the oligonucleotides will be closely related, differing only in the choice of codons for alternate amino acids selected for variation at 09. The recombination-based diversity generation mechanism may be performed for one or multiple cycles. If multiple cycles are used, each involves a screening step to identify which variants have acceptable performance to be used in a next recombination cycle. This is a form of directed evolution.

In a different example, a "reference" protein sequence is chosen and the residues selected at 09 are "toggled" to identify individual members of the variant library. The new proteins so identified are synthesized by an appropriate technique to generate the new library. In one example, the reference sequence may be a top-performing member of the training set or a "best" sequence predicted by a PLS or PCR model.

In another approach, the sequence activity model is used as a "fitness function" in a genetic algorithm for exploring sequence space. After one or more rounds of the genetic algorithm (with each round using the fitness function to select one or more possible sequences for a genetic operation), a next generation library is identified for use as described in this flow chart. In a very real sense this strategy can be viewed as in silico directed evolution. In an ideal case, if one had in hand an accurate, precise global or local fitness function one could perform all the evolution in silico and synthesize a single best variant for use in the final commercial or research application. Though this is likely to be impossible to achieve in most cases such a view of the process lends clarity to the goals and approach of using machine learning techniques for directed evolution.

After the new library has been produced, it is screened for activity, as indicated in a block 13. Ideally, the new library will present one or more members with better activity than was observed in the previous library. However, even without such advantage, the new library can provide beneficial information. Its members may be employed for generating improved models that account for the effects of the variations selected in 09, and thereby more accurately predict activity across wider regions of sequence space. Further, the library may represent a passage in sequence space from a local maximum toward a global maximum (in activity).

Depending on the goal of process 01, it may be desirable to generate a series of new protein variant libraries, with each one providing new members of a training set. The updated training set is then used to generate an improved model. To this end, process 01 is shown with a decision operation 15, which determines whether yet another protein variant library should be produced. Various criteria can be used to make this decision. Examples include the number of protein variant libraries generated so far, the activity of top proteins from the current library, the magnitude of activity desired, and the level of improvement observed in recent new libraries.

Assuming that the process is to continue with a new library, the process returns to operation 05 where a new sequence-activity model is generated from sequence and activity data obtained for the current protein variant library. In other words, the sequence and activity data for the current protein variant library serves as part of the training set for the new model (or it may serve as the entire training set). Thereafter, operations 07, 09, 11, 13, and 15 are performed as described above, but with the new model.

At some point, in process 01, this cycle will end and no new library will be generated. At that point, the process may simply terminate or one or more sequences from one or more of the libraries may be selected for development and/or manufacture. See block 17.

A. Choosing Protein Variant Libraries

Protein variant libraries are groups of multiple proteins having one or more residues that vary from member to member in a library. They may be generated by methods of this invention. They may provide the data for training sets used to generate sequence-activity models in accordance with this invention. The number of proteins included in a protein variant library depends on the application and the cost.

In one example, the protein variant library is generated from one or more naturally occurring proteins, which may be protein members encoded by a single gene family. Other starting points for the library may be used. From these seed or starting proteins, the library may be generated by various techniques. In one case, the library is generated by DNA fragmentation-mediated recombination as described in Stemmer (1994) Proc. Natl. Acad. Sci. USA 10747-10751 and WO 95/22625, synthetic oligonucleotide-mediated recombination as described in Ness et al. (2002) Nature Biotechnology 20:1251-1255 and WO 00/42561) on nucleic acids encoding part or all of one or more parent proteins. A combination of these methods may be used as well (i.e., recombination of DNA fragments and synthetic oligonucleotides) as well as other recombination-based methods described in, for example, WO97/20078 and WO98/27230.

In another case, a single starting sequence is modified in various ways to generate the library. Preferably the library is generated by systematically varying the individual residues of the starting sequence. In one example, a design of experiment (DOE) methodology is employed to identify the systematically varied sequences. In another example, a "wet lab" procedure such as oligonucleotide-mediated recombination is used to introduce some level of systematic variation.

As used herein, the term "systematically varied sequences" refers to a set of sequences in which each residue is seen in multiple contexts. In principle, the level of systematic variation can be quantified by the degree to which the sequences are orthogonal from one another (maximally different compared to the mean). In practice, the process does not depend on having maximally orthogonal sequences, however, the quality of the model will be improved in direct relation to the orthogonality of the sequence space tested. In a simple example, a peptide sequence is systematically varied by identifying two residue positions, each of which can have one of two different amino acids. A maximally diverse library includes all four possible sequences. Such maximal systematic variation increases exponentially with the number of variable positions; e.g., by $2^N$, when there are 2 options at each of N residue positions. Those having ordinary skill in the art will readily recognize that maximal systematic variation, however, is not required by the invention methods. Systematic variation provides a mechanism for identifying a relatively small set of sequences for testing that provides a good sampling of sequence space.

Protein variants having systematically varied sequences can be obtained in a number of ways using techniques that are well known to those having ordinary skill in the art. As indicated, suitable methods include recombination-based methods that generate variants based on one or more "parental" polynucleotide sequences. Polynucleotide sequences can be recombined using a variety of techniques, including, for example, DNAse digestion of polynucleotides to be recombined followed by ligation and/or PCR reassembly of the nucleic acids. These methods include those described in, for example, Stemmer (1994) Proc. Natl. Acad. Sci. USA, 91:10747-10751, U.S. Pat. No. 5,605,793, "Methods for In Vitro Recombination," U.S. Pat. No. 5,811,238, "Methods for Generating Polynucleotides having Desired Characteristics by Iterative Selection and Recombination," U.S. Pat. No. 5,830,721, "DNA Mutagenesis by Random Fragmentation and Reassembly," U.S. Pat. No. 5,834,252, "End Complementary Polymerase Reaction," U.S. Pat. No. 5,837,458, "Methods and Compositions for Cellular and Metabolic Engineering," "WO98/42832, "Recombination of Polynucleotide Sequences Using Random or Defined Primers," WO 98/27230, "Methods and Compositions for Polypeptide Engineering," WO 99/29902, "Method for Creating Polynucleotide and Polypeptide Sequences," and the like.

Synthetic recombination methods are also particularly well suited for generating protein variant libraries with systematic variation. In synthetic recombination methods, a plurality of oligonucleotides are synthesized which collectively encode a plurality of the genes to be recombined. Typically the oligonucleotides collectively encode sequences derived from homologous parental genes. For example, homologous genes of interest are aligned using a sequence alignment program such as BLAST (Atschul, et al., *J. Mol. Biol.*, 215:403-410 (1990). Nucleotides corresponding to amino acid variations between the homologues are noted. These variations are optionally further restricted to a subset of the total possible variations based on covariation analysis of the parental sequences, functional information for the parental sequences, selection of conservative or non-conservative changes between the parental sequences, or other like criteria. Variations are optionally further increased to encode additional amino acid diversity at positions identified by, for example, covariation analysis of the parental sequences, functional information for the parental sequences, selection of conservative or non-conservative changes between the parental sequences, or apparent tolerance of a position for variation. The result is a degenerate gene sequence encoding a consensus amino acid sequence derived from the parental gene sequences, with degenerate nucleotides at positions encoding amino acid variations. Oligonucleotides are designed which contain the nucleotides required to assemble the diversity present in the degenerate gene. Details regarding such approaches can be found in, for example, Ness et al. (2002), *Nature Biotechnology* 20:1251-1255, WO 00/42561, "Oligonucleotide Mediated Nucleic Acid Recombination," WO 00/42560, "Methods for Making Character Strings, Polynucleotides and Polypeptides having Desired Characteristics," WO 01/75767, "In Silico Cross-Over Site Selection," and WO 01/64864, "Single-Stranded Nucleic Acid Template-Mediated Recombination and Nucleic Acid Fragment Isolation." The identified polynucleotide variant sequences may be transcribed and translated, either in vitro or in vivo, to create a set or library of protein variant sequences.

The set of systematically varied sequences can also be designed a priori using design of experiment (DOE) methods to define the sequences in the data set. A description of DOE methods can be found in Diamond, W. J. (2001) *Practical Experiment Designs: for Engineers and Scientists*, John Wiley & Sons and in "Practical Experimental Design for engineers and scientists" by William J Drummond (1981) Van Nostrand Reinhold Co New York, "Statistics for experimenters" George E. P. Box, William G Hunter and J. Stuart Hunter (1978) John Wiley and Sons, New York, or, e.g., on the world wide web at itl.nist.gov/div898/handbook/. There are several computational packages available to perform the relevant mathematics, including Statistics Toolbox (MatLab), JMP, Statistica and Statease Design expert. The result is a systematically varied and orthogonal dispersed data set of sequences that is suitable for building the sequence activity model of the present invention. DOE-based data sets can be readily generated using either Plackett-Burman or Fractional Factorial designs. Id.

In engineering and chemical sciences, fractional factorial designs, for example, are used to define fewer experiments (than in full factorial designs) in which a factor is varied (toggled) between two or more levels. Optimization techniques are used to ensure that the experiments chosen are maximally informative in accounting for factor space variance. The same design approaches (e.g., fractional factorial, D-optimal design) can be applied in protein engineering to construct fewer sequences where a given number of positions are toggled between two or more residues. This set of sequences would be an optimal description of systematic variance present in the protein sequence space in question.

An example of the DOE approach applied to protein engineering includes the following operations:

1) Identify positions to toggle based on the principles described earlier (present in parental sequences, level of conservation, etc.)
2) Create a DOE experiment using one of the commonly available statistical packages by defining the number of factors (variable positions), the number of levels (choices at each position), and the number of experiments to run. The information content of the output matrix (typically consisting of 1s and 0s that represent residue choices at each position) depends directly on the number of experiments to run (the more the better).
3) Use the output matrix to construct a protein alignment that codes the 1s and 0s back to specific residue choices at each position.
4) Synthesize the genes encoding the proteins represented in the protein alignment.
5) Test the proteins encoded by the synthesized genes in relevant assay(s).
6) Build a model on the tested genes/proteins.
7) Follow the steps described before to identify positions of importance and to build a subsequent library with improved fitness.

For example purposes, consider a protein in which the functionally best amino acid residues at 20 positions are to be determined, e.g., where there are 2 possible amino acids available at each position. In this case, a resolution IV factorial design would be appropriate. A resolution IV design is defined as one which is capable of elucidating the effects of all single variables, with no two-factor effects overlapping them. The design would then specify a set of 40 specific amino acid sequences that would cover the total diversity of $2^{20}$ (~1 million) possible sequences. These sequences are then generated by a standard gene synthesis protocol and the function and fitness of these clones is determined.

An alternative to the above approaches is to employ all available sequences, e.g., the GenBank® database and other public sources, to provide the protein variant library. Although this entails massive computational power, current technologies make the approach feasible. Mapping all available sequences provides an indication of sequence space regions of interest.

B. Generating a Sequence Activity Model & Using that Model to Identify Residue Positions for Variation As indicated above, a sequence-activity model used with the present invention relates protein sequence information to protein activity. The protein sequence information used by the model may take many forms. Frequently, it is a complete sequence of the amino acid residues in a protein; e.g., HGPVFSTGGA . . . . In some cases, however, it may be unnecessary to provide the complete amino acid sequence. For example, it may be sufficient to provide only those residues that are to be varied in a particular research effort. At later stages in research, for example, many residues may be fixed and only limited regions of sequence space remain to be explored. In such situations, it may be convenient to provide sequence activity models that require, as inputs, only the identification of those residues in the regions of the protein where the exploration continues. Still further, some models may not require exact identities of residues at the residue positions, but instead identify one or more physical or chemical properties that characterize the amino acid at a particular residue position. For example, the model may require specification of residue positions by bulk, hydrophobicity, acidity, etc. In some models, combinations of such properties are employed.

The form of the sequence-activity model can vary widely, so long as it provides a vehicle for correctly approximating the relative activity of proteins based on sequence information. Generally, it will treat activity as a dependent variable and sequence/residue values as independent variables. Examples of the mathematical/logical form of models include linear and non-linear mathematical expressions of various orders, neural networks, classification and regression trees/graphs, clustering approaches, recursive partitioning, support vector machines, and the like. In one preferred embodiment, the model form is a linear additive model in which the products of coefficients and residue values are summed. In another preferred embodiment, the model form is a non-linear product of various sequence/residue terms, including certain residue cross products (which represent interaction terms between residues).

Models are developed from a training set of activity versus sequence information to provide the mathematical/logical relationship between activity and sequence. This relationship is typically validated prior to use for predicting activity of new sequences or residue importance.

Various techniques for generating models are available. Frequently, such techniques are optimization or minimization techniques. Specific examples include partial least squares, various other regression techniques, as well as genetic programming optimization techniques, neural network techniques, recursive partitioning, support vector machine techniques, CART (classification and regression trees), and/or the like. Generally, the technique should produce a model that can distinguish residues that have a significant impact on activity from those that do not. Preferably, the model should also rank individual residues or residue positions based on their impact on activity.

In one important class of techniques, models are generated by a regression technique that identifies covariation of independent and dependent variables in a training set. Various regression techniques are known and widely used. Examples include multiple linear regression (MLR), principal component regression (PCR) and partial least squares regression (PLS).

MLR is the most basic of these techniques. It simply solves a set of coefficient equations for members of a training set. Each equation relates to the activity of a training set member (dependent variable) with the presence or absence of a particular residue at a particular position (independent variables). Depending upon the number of residue options in the training set, these expressions can be quite large.

Like MLR, PLS and PCR generate models from equations relating sequence activity to residue values. However, these techniques do so in a different manner. They first perform a coordinate transformation to reduce the number of independent variables. They then perform the regression on the transformed variables. In MLR, there are a potentially very large number of independent variables: two or more for each residue position that varies within the training set. Given that proteins and peptides of interest are often quite large and the training set may provide many different sequences, the number of independent variables can quickly become very large. By reducing the number of variables to focus on those that provide the most variation in the data set, PLS and PCR generally require fewer samples and simplify the problem of generating a model.

PCR is similar to PLS regression in that the actual regression is done on a relatively small number of latent variables obtained by coordinate transformation of the raw independent variables (residue values). The difference between PLS and PCR is that the latent variables in PCR are constructed by maximizing covariation between the independent variables (residue values). In PLS regression, the latent variables are constructed in such a way as to maximize the covariation between the independent variables and the dependent variables (activity values). Partial Least Squares regression is described in Hand, D. J., et al. (2001) *Principles of Data Mining (Adaptive Computation and Machine Learning)*, Boston, Mass., MIT Press, and in in Geladi, et al. (1986) "Partial Least-Squares Regression: a Tutorial," *Anal. Chim. Acta,* 198:1-17. Both of these references are incorporated herein by reference for all purposes.

In PCR and PLS, the direct result of the regression is an expression for activity that is a function of the weighted latent variables. This expression can be transformed to an expression for activity as a function of the original independent variables by performing a coordinate transformation that converts the latent variables back to the original independent variables.

In essence, both PCR and PLS first reduce the dimensionality of the information contained in the training set and then perform a regression analysis on a transformed data set; which has been transformed to produce new independent variables, but preserves the original dependent variable values. The transformed versions of the data sets may result in only a relatively few expressions for performing the regression analysis. Compare this with a situation where no dimension reduction is performed. In that situation, each separate residue for which there can be a variation must be considered. This can be a very large set of coefficients; $2^N$ coefficients, where N is the number of residue positions that may vary in the training set. In a typical principal component analysis, only 3, 4, 5, 6 principal components are employed.

The ability of machine learning techniques to fit the training data is often referred to as the "model fit" and in regression techniques such as MLR, PCR and PLS is typically measured by the sum squared difference between measured and predicted values. For a given training set, the optimal model fit will always be achieved using MLR, with PCR and PLS often having a worse model fit (higher sum squared error between measurements and predictions). However, the chief advantage of using latent variable regression techniques such as PCR and PLS lies in the predictive ability of such models. Obtaining a model fit with very small sum squared error in no way guarantees the model will be able to accurately predicted new samples not seen in the training set—in fact, it is often the opposite case, particularly when there are many variables and only a few observations (samples). Thus latent variable regression techniques (PCR, PLS) while often having worse model fits on the training data are usually more robust and are able to predict new samples outside the training set more accurately.

Another class of tools that can be used to generate models in accordance with this invention is the support vector machines. These mathematical tools take as inputs training sets of sequences that have been classified into two or more groups based on activity. Support vector machines operate by weighting different members of a training set differently depending upon how close they are to a hyperplane interface separating "active" and "inactive" members of the training set. This technique requires that the scientist first decide which training set members to place in the active group and which training set members to place in the inactive group. This may be accomplished by choosing an appropriate numerical value of activity to serve as the boundary between active and inactive members of the training set. From this classification, the support vector machine will generate a vector, W, that can provide coefficient values for individual ones of the independent variables defining the sequences of the active and inactive group members in the training set. These coefficients can be used to "rank" individual residues as described elsewhere herein. The technique attempts to identify a hyperplane that maximizes the distance between the closest training set members on opposite sides of that plane. In another variation, support vector regression modeling is carried out. In this case, the dependent variable is a vector of continuous activity values. The support vector regression model will generate a coefficient vector, W, which can be used to rank individual residues.

SVMs have been used to look at large data sets in many studies and have been quite popular in the DNA microarray field. Their potential strengths include the ability to finely discriminate (by weighting) which factors separate samples from each other. To the extent that an SVM can tease out precisely which residues contribute to function, it can be a particularly useful tool for ranking residues in accordance with this invention. SVMs are described in S. Gunn (1998) "Support Vector Machines for Classification and Regressions," Technical Report, Faculty of Engineering and Applied Science, Department of Electronics and Computer Science, University of Southampton, which is incorporated herein by reference for all purposes.

Another model generation technique of interest is genetic programming. This technique employs a Darwinian style evolution to discover the formulae and rules that characterize the data of a training set. It can be used in regression problems of the types described herein. The underlying effect can be linear or non-linear. Genetic programming is described in R. Goodacre et al. (2000) "Detection of the Dipicolinic Acid Biomarker in *Bacillus* Spores Using Curie-Point Pyrolysis Mass Spectrometry and Fourier Transform Infrared Spectroscopy,"*Anal. Chem.,* 72, 119-127, which is incorporated herein by reference for all purposes. Examples of software tools for performing genetic programming include the "GMAX" and the "GMAX-Bio" available from Aber Genomic Computing Ltd of Wales, UK.

i) Linear Model Examples

While the present invention is directed to non-linear models, these may be more easily understood in the context of linear models of sequence versus activity. Thus, the form and development of linear models will now be described. In general, a linear regression model of activity versus sequence has the following form:

$$y = c_0 + \sum_{i=1}^{N}\sum_{j=1}^{M} c_{ij} x_{ij} \quad (1)$$

In this linear expression, y is predicted response, while $c_{ij}$ and $x_{ij}$ are the regression coefficient and bit value or dummy variable used to represent residue choice, respectively at position i in the sequence. There are N residue positions in the sequences of the protein variant library and each of these may be occupied by one or more residues. At any given position, there may be j=1 through M separate residue types. This model assumes a linear (additive) relationship between the residues at every position. An expanded version of equation 1 follows:

$$y = c_0 + c_{11}x_{11} + c_{12}x_{12} + \ldots c_{1M}x_{1M} + c_{21}x_{21} + c_{22}x_{22} + \ldots c_{2M}x_{2M} + \ldots + c_{NM}x_{NM}$$

As indicated, data in the form of activity and sequence information is derived from the initial protein variant library and used to determine the regression coefficients of the model. The dummy variables are first identified from an alignment of the protein variant sequences. Amino acid residue positions are identified from among the protein variant sequences in which the amino acid residues in those positions differ between sequences. Amino acid residue information in some or all of these variable residue positions may be incorporated in the sequence activity model.

Table I contains sequence information in the form of variable residue positions and residue types for 10 illustrative variant proteins, along with activity values corresponding to each variant protein. Understand that these are representative members of a larger set that is required to generate enough equations to solve for all the coefficients. Thus, for example, for the illustrative protein variant sequences in Table I, positions 10, 166, 175, and 340 are variable residue positions and all other positions, i.e., those not indicated in the Table, contain residues that are identical between Variants 1-10.

TABLE I

Illustrative Sequence and Activity Data

| | Variable Positions: | | | |
|---|---|---|---|---|
| | 10 | 166 | 175 | 340 | y (activity) |
| Variant 1 | Ala | Ser | Gly | Phe | $y_1$ |
| Variant 2 | Asp | Phe | Val | Ala | $y_2$ |
| Variant 3 | Lys | Leu | Gly | Ala | $y_3$ |
| Variant 4 | Asp | Ile | Val | Phe | $y_4$ |
| Variant 5 | Ala | Ile | Val | Ala | $y_5$ |
| Variant 6 | Asp | Ser | Gly | Phe | $y_6$ |
| Variant 7 | Lys | Phe | Gly | Phe | $y_7$ |
| Variant 8 | Ala | Phe | Val | Ala | $y_8$ |
| Variant 9 | Lys | Ser | Gly | Phe | $y_9$ |
| Variant 10 | Asp | Leu | Val | Ala | $y_{10}$ |
| and so on. | | | | |

Thus, based on equation 1, a regression model can be derived from the systematically varied library in Table I, i.e.:

$$y = c_0 + c_{10Ala}x_{10Ala} + c_{10Asp}x_{10Asp} + c_{10Lys}x_{10Lys} + c_{166Ser}x_{166Ser} + \quad (2)$$
$$c_{166Phe}x_{166Phe} + c_{166Leu}x_{166Leu} + c_{166Ile}x_{166Ile} + c_{175Gly}x_{175Gly} +$$
$$c_{175Val}x - 175Val + c_{340Phe}x_{340Phe} + c_{340Ala}x_{340Ala}$$

The bit values (x dummy variables) can be represented as either 1 or 0 reflecting the presence or absence of the designated amino acid residue or alternatively, 1 or −1, or some other surrogate representation. For example, using the 1 or 0 designation, $x_{10Ala}$ would be "1" for Variant 1 and "0" for Variant 2. Using the 1 or −1 designation, $x_{10Ala}$ would be "1" for Variant 1 and "−1" for Variant 2. The regression coefficients can thus be derived from regression equations based on the sequence activity information for all variants in library. Examples of such equations for Variants 1-10 (using the 1 or 0 designation for x) follow:

$y_1 = c_0 + c_{10Ala}(1) + c_{10Asp}(0) + c_{10Lys}(0) + c_{166ser}(1) + c_{166Phe}(0) +$
$\quad c_{166Leu}(0) + c_{166Ile}(0) + c_{175Gly}(1) + c_{175Val}(0) + c_{340Phe}(1) + c_{340Ala}(0)$ $y_2 = c_0 + c_{10Ala}(0) + c_{10Asp}(1) + c_{10Lys}(0) + c_{166Ser}(0) + c_{166Phe}(1) +$
$\quad c_{166Leu}(0) + c_{166Ile} + c_{175Gly}(0) + c_{175Val}(1) + c_{340Phe}(0) + c_{340Ala}(1)$ $y_3 = c_0 + c_{10Ala}(0) + c_{10Asp}(0) + c_{10Lys}(1) + c_{166Ser}(0) + c_{166Phe}(0) +$
$\quad c_{166Leu}(1) + c_{166Ile}(0) + c_{175Gly}(1) + c_{175Val}(0) + c_{340Phe}(0) + c_{340Ala}(1)$ $y_4 = c_0 + c_{10Ala}(0) + c_{10Asp}(1) + c_{10Lys}(0) + c_{166Ser}(0) + c_{166Phe}(0) +$
$\quad c_{166Leu}(0) + c_{166Ile}(1) + c_{175Gly}(0) + c_{175Val}(1) + c_{340Phe}(1) + c_{340Ala}(0)$ $y_5 = c_0 + c_{10Ala}(1) + c_{10Asp}(0) + c_{10Lys}(0) + c_{166Ser}(0) + c_{166Phe}(0) +$
$\quad c_{166Leu}(0) + c_{166Ile}(1) + c_{175Gly}(0) + c_{175Val}(1) + c_{340Phe}(0) + c_{340Ala}(1)$ $y_6 = c_0 + c_{10Ala}(0) + c_{10Asp}(1) + c_{10Lys}(0) + c_{166Ser}(1) + c_{166Phe}(0) +$
$\quad c_{166Leu}(0) + c_{166Ile}(0) + c_{175Gly}(1) + c_{175Val}(0) + c_{340Phe}(1) + c_{340Ala}(0)$ $y_7 = c_0 + c_{10Ala}(0) + c_{Asp}(0) + c_{10Lys}(1) + c_{166Ser}(0) + c_{166Phe}(1) +$
$\quad c_{166Leu}(0) + c_{166Ile}(0) + c_{175Gly}(1) + c_{175Val}(0) + c_{340Phe}(1) + c_{340Ala}(0)$ $y_8 = c_0 + c_{10Ala}(1) + c_{10Asp}(0) + c_{10Lys}(0) + c_{166Ser}(0) + c_{166Phe}(1) +$
$\quad c_{166Leu}(0) + c_{166Ile}(0) + c_{175Gly}(0) + c_{175Val}(1) + c_{340Phe}(0) + c_{340Ala}(1)$ $y_9 = c_0 + c_{10Ala}(0) + c_{10Asp}(0) + c_{10Lys}(1) + c_{166Ser}(1) + c_{166Phe}(0) +$
$\quad c_{166Leu}(0) + c_{166Ile}(0) + c_{175Gly}(1) + c_{175Val}(0) + c_{340Phe}(1) + c_{340Ala}(0)$ $y_{10} = c_0 + c_{10Ala}(0) + c_{10Asp}(1) + c_{10Lys}(0) + c_{166Ser}(0) + c_{166Phe}(0) +$
$\quad c_{166Leu}(1) + c_{166Ile}(0) + c_{175Gly}(0) + c_{175Val}(1) + c_{340Phe}(0) + c_{340Ala}(1)$ The complete set of equations can be readily solved using a regression technique (e.g., PCR, PLS, or MLR) to determine the value for regression coefficients corresponding to each residue and position of interest. In this example, the relative magnitude of the regression coefficient correlates to the relative magnitude of contribution of that particular residue at the particular position to activity. The regression coefficients may then be ranked or otherwise categorized to determine which residues are more likely to favorably contribute to the desired activity. Table II provides illustrative regression coefficient values corresponding to the systematically varied library exemplified in Table I:

TABLE II

Illustrative Rank Ordering of Regression Coefficients

| REGRESSION COEFFICIENT | VALUE |
| --- | --- |
| $c_{166 Ile}$ | 62.15s |
| $c_{175 Gly}$ | 61.89 |
| $c_{10 Asp}$ | 60.23 |
| $c_{340 Ala}$ | 57.45 |
| $c_{10 Ala}$ | 50.12 |
| $c_{166 Phe}$ | 49.65 |
| $c_{166 Leu}$ | 49.42 |
| $c_{340 Phe}$ | 47.16 |
| $c_{166 Ser}$ | 45.34 |
| $c_{175 Val}$ | 43.65 |
| $c_{10 Lys}$ | 40.15 |

The rank ordered list of regression coefficients can be used to construct a new library of protein variants that is optimized with respect to a desired activity (i.e., improved fitness). This can be done in various ways. In one case, it is accomplished by retaining the amino acid residues having coefficients with the highest observed values. These are the residues indicated by the regression model to contribute the most to desired activity. If negative descriptors are employed to identify residues (e.g., 1 for leucine and −1 for glycine), it becomes necessary to rank residue positions based on absolute value of the coefficient. Note that in such situations, there is typically only a single coefficient for each residue. The absolute value of the coefficient magnitude gives the ranking of the corresponding residue position. Then, it becomes necessary to consider the signs of the individual residues to determine whether each of them is detrimental or beneficial in terms of the desired activity.

ii) Non-Linear Models

Non-linear modeling is employed to account for residue-residue interactions that contribute to activity in proteins. An N-K landscape describes this problem. The parameter N refers to the number of variable residues in a collection of related polypeptides sequences. The parameter K represents the interaction between individual residues within anyone of these polypeptides. Interaction is usually a result of close physical proximity between various residues whether in the primary, secondary, or tertiary structure of the polypeptide. The interaction may be due to direct interactions, indirect interactions, physicochemical interactions, interactions due to folding intermediates, translational effects, and the like.

The parameter K is defined such that for value K=1, each variable residue (e.g., there are 20 of them) interacts with exactly one other residue in its sequence. In the case where all residues are physically and chemically separate from the effects of all other residues, the value of K is zero. Obviously, depending upon the structure of the polypeptide, K can have a wide range of different values. With a rigorously solved structure of the polypeptide in question, a value for K may be estimated. Often, however, this is not the case.

A purely linear, additive model of polypeptide activity (as described above) can be improved by including one or more non-linear interaction terms representing specific interactions between 2 or more residues. In the context of the model form presented above, these terms are depicted as "cross-products" containing two or more dummy variables representing the two or more particular residues (each associated with a particular position in the sequence) that interact to have a significant positive or negative impact on activity. For example, a cross-product term may have the form $c_{ab}x_a x_b$, where $x_a$ is a dummy variable representing the presence of a particular residue at a particular position on the sequence and the variable $x_b$ represents the presence of a particular residue at a different position (that interacts with the first position) in the polypeptide sequence. A detailed example form of the model is shown below.

The presence of all residues represented in the cross-product term (each of two or more specific types of residue at specifically identified positions) impacts the overall activity of the polypeptide. The impact can be manifest in many different ways. For example, each of the individual interacting residues when present alone in a polypeptide may have a negative impact on activity, but when each of them is present together in the polypeptide, the overall effect is positive. The opposite may be true in other cases. In addition, there may be a synergistic effect produced in which each of the individual residues alone has a relatively limited impact on activity, but when all of them are present the effect on activity is greater than the cumulative effects of all the individual residues.

It is possible that a non-linear model could include a cross-product term for every possible combination of interacting variable residues in the sequence. However, this would not represent physical reality, as only a subset of the variable residues actually interact with one another. In addition, it would result in "overfitting" to produce a model that provides spurious results that are manifestations of the particular polypeptides used to create the model and do not represent real interactions within the polypeptide. The correct number of cross-product terms for a model that represents physical reality, and avoids overfitting, is dictated by the value of K. For example, if K=1, the number of cross-product interaction terms equals N.

Note that in general, it may be more preferable to have too few cross-product terms than too many. If the relatively few cross-product terms included in the non-linear model are actually those having the biggest influence on activity, than it is definitely preferable to have too few. As should be apparent, in constructing a non-linear model, it is important to identify those cross-product interaction terms representing true structural interactions that have a significant impact on activity. This can be accomplished in various ways. These include forward addition, where candidate cross-product terms (starting with the term with largest regression coefficient and progressing to terms with smaller regression coefficients) are added to the initial linear only model one at a time until the addition of terms is no longer statistically significant (as measured by an F-test or some other appropriate statistical test); reverse elimination, where all possible cross product terms are added at the beginning and removed one at a time (starting with the term with smallest regression coefficient and progressing to terms with larger regression coefficients) until removal the least important remaining term is statistically significant. One example presented below involves the use of a genetic algorithm to identify the useful non-linear terms.

Generally, the approach to generating a non-linear model containing such interaction terms is the same as the approach described above for generating a linear model. In other words, a training set is employed to "fit" the data to a model. However, one or more non-linear terms, preferably the cross-product terms discussed above, are added to the form of the model. Further, the resulting non-linear model, like the linear models described above, can be employed to rank the importance of various residues on the overall activity of a polypeptide. Various techniques can identify the best combination of variable residues as predicted by the non-linear equation. Unfortunately, unlike the linear case, it is often impossible to accomplish this by simple inspection of the additive model. Approaches to ranking the residues are described below.

Note that there are a very large number of possible cross-product terms for variable residues, even when limited to interactions caused by only two residues. As more interactions occur, the number of potential interactions to consider for a non-linear model grows in an exponential manner. If the model includes the possibility of interactions that include three or more residues, the number of potential terms grows even more rapidly.

In a simple case where there are 20 variable residues and K=1 (assumes that each variable residue interacts with one other variable residue), there should be 20 interaction terms (cross-products) in the model. If there are any fewer, the model will not fully describe the interactions (although some of the interactions may not have a significant impact on activity), and any more and the model may overfit the data set. There are $N*(N-1)/2$ or 190 possible pairs of interactions. Finding the combination of 20 unique pairs that describe the 20 interactions in the sequence is a significant computational problem. There are approximately $5.48 \times 10^{26}$ possible combinations.

Numerous techniques can be employed to identify the relevant cross-product terms. Depending upon the size of the problem and the computational power available, one might be able to explore all possible combinations and thereby identify the one model that best fits the data (the numbers of the training set). However, often the problem will be too large for the available computational resources and so one must resort to an efficient search algorithm or an approximation. As mentioned, one suitable search technique is a genetic algorithm.

Figure 2:
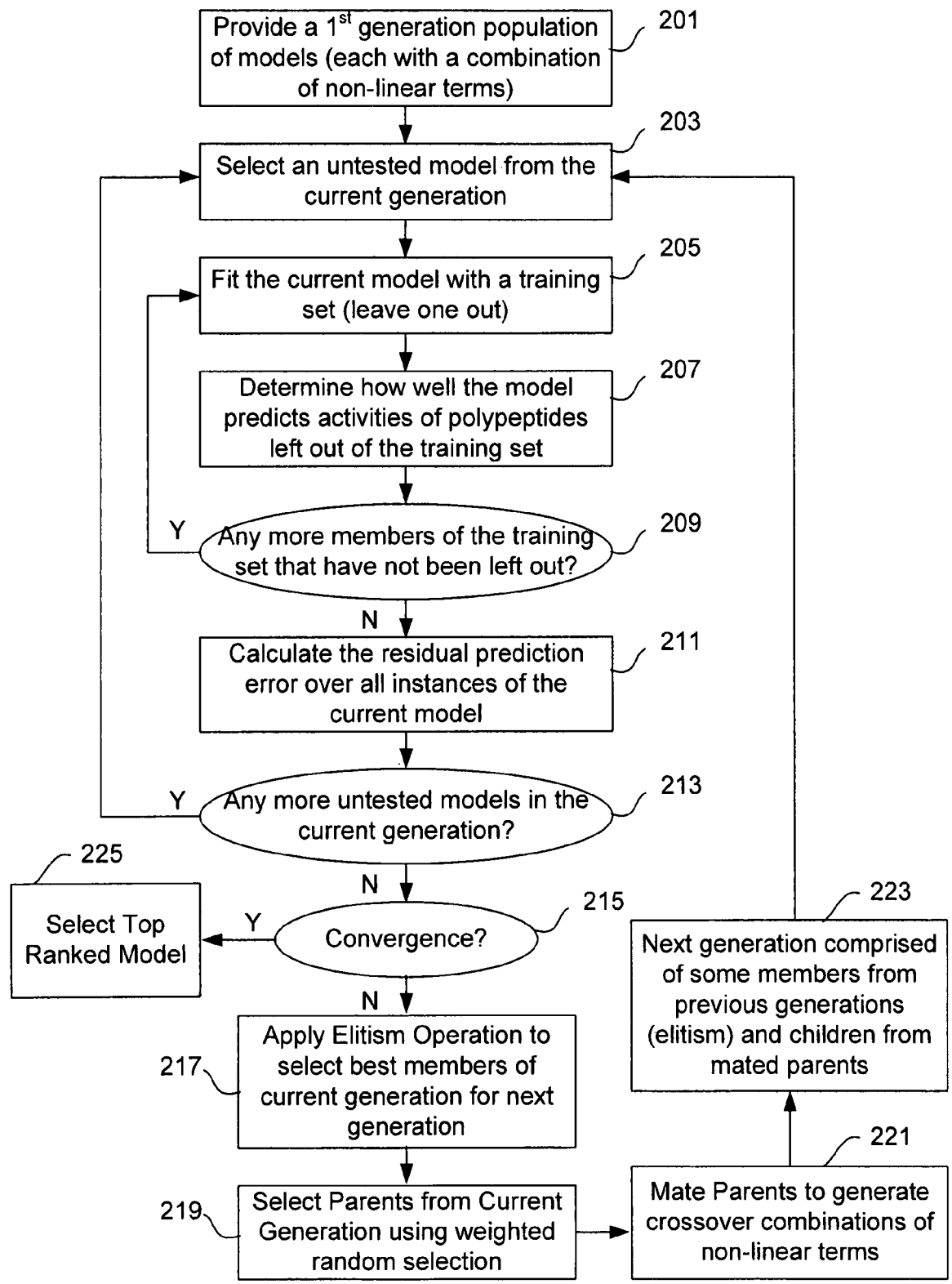
FIG. 2 is a flow chart depicting a genetic algorithm for selecting non-linear cross product terms in accordance with an embodiment of this invention.

In a genetic algorithm, an appropriate fitness function and an appropriate mating procedure are defined. The fitness function provides a criterion for determining which models (combinations of cross-product terms) are "most fit" (i.e., likely to provide the best results). The mating procedure provides a mechanism for introducing new combinations of cross-product terms from successful "parental" models in a previous generation. One example of a genetic algorithm for identifying a combination of cross-product terms will now be described with reference to FIG. 2. This algorithm begins with a first generation comprising multiple possible models, some of which do a better job of representing physical reality than others. See block 201. The first and each successive generation is represented as a number of models in a "population". Each "model" is a combination of linear terms (fixed across all models) and non-linear cross-product terms. The "model" in this genetic algorithm does not intrinsically include coefficients for the individual linear and non-linear terms, only an identification of a combination of non-linear terms (e.g., the cross-product terms). The genetic algorithm proceeds towards convergence by marching through successive generations of models, each characterized by a different combination of non-linear interaction terms.

Each model in a generation is used to fit a training set of polypeptides (having known sequences and associated activities). The training set is used to fit the individual models of the current generation. See block 203, 205, 207, and 209 of FIG. 2. In one example, a partial least squares technique or similar regression technique is used to perform the fit.

The predictive power of the resulting model (including coefficients obtained by the regression on the training set data) is used as a fitting function. To provide a detailed assessment of the predictive power, many different fits of a model may be provided for a given training set. See blocks 205, 207, and 209. Each fit provides its own unique set of coefficient values for the linear and non-linear terms of the model under consideration. In one approach, a "leave one out" approach is employed in which all but one member of the training set is used to fit the model. This left out member is then used to test the predictive power of the resulting instance of the model. The model instance (model terms together coefficient values identified by fitting) is expected to do a good job of predicting the activities of the training set members employed to produce it. However, it may not do so well at predicting the activity of a polypeptide from outside the utilized members of the training set. In a specific embodiment, multiple "leave one out" model instances are generated and each is assessed for its ability to predict the activity of the left out member. The resulting set of predictions is combined to get an aggregate measure of the predictive capability (see block 211). In one example, the aggregate measure is a predicted residual sum of squares (PRESS) for the various leave one out model instances of the current model. The PRESS is, in effect, the fitting function of the genetic algorithm.

After each combination of non-linear cross-product terms (model) in a particular generation is evaluated for its predictive power (i.e., decision 213 is answered in the negative), the genetic algorithm is checked for convergence. See block 215. Assuming that the genetic algorithm has not yet converged, the models of the current generation are ranked. Those that do the best job of predicting activity may be preserved and used in the next generation. See block 217. For example, an elitism rate of 10% may be employed. In other words, the top 10% of models (as determined using the fitting function and measured by, e.g., PRESS scores) are set aside to become members of the next generation. The remaining 90% of the members in the next generation are obtained by mating "parents" from the previous generation. See blocks 219, 221, and 223.

The "parents" are models selected randomly from the previous generation. See block 219. However, the random selection is typically weighted toward more fit numbers of the previous generation. For example, the parent models may be selected using a linear weighting (e.g., a model that performs 1.2 times better than another model is 20% more likely to be selected) or a geometric weighting (i.e., the predictive differences in models are raised to a power in order to obtain a probability of selection).

After a set of parent models has been selected, pairs of such models are mated (block 221) to produce children models by providing some non-linear terms from one parent and other non-linear terms form the other parent. In one approach, the non-linear terms (cross-products) of the two parents are aligned and each term is considered in succession to determine whether the child should take the term from parent A or from parent B. In one implementation, the mating process begins with parent A and randomly determines whether a "cross over" event should occur at the first non-linear term encountered. If so, the term is taken from parent B. If not, the term is taken from parent A. The next term in succession is considered for cross over, etc. The terms continue to come from the parent donating the previous term under consideration until a cross over event occurs. At that point, the next term is donated from the other parent and all successive terms are donated from that parent until another cross over event occurs. To ensure that the same non-linear cross-product terms is not selected at two different locations in the child model, various techniques may be employed, e.g., a partially matched cross over technique.

After each non-linear term has been considered, a child "model" is defined for the next generation. Then another two parents are chosen to produce another child model, and so on. Eventually, after a complete generation has been selected in this manner (block 223), the next generation is ready for evaluation, and process control then returns to block 203, where the members of the next generation are evaluated as described above.

The process continues generation-by-generation until convergence, (i.e., decision block 215 is answered in the negative. At that point, the top ranked model is selected from the current generation as the overall best model. See block 225. Convergence can be tested by many conventional techniques. Generally, it involves determining that the performance of the best model from a number of successive generations does not change appreciably.

At this point, an example will be presented to show the value of incorporating non-linear cross-product terms in a model predicting activity from sequence. Consider the following non-linear model in which it is assumed there are only two residue options at each variable position in the sequence. In this example, the protein sequence is cast into a coded sequence by using dummy variables that correspond to choice A or choice B, using +1 and −1 respectively. The model is immune to the arbitrary choice of which numerical value used to assign each residue choice.

TABLE III

| | Variable Position | | | | | | | | | |
|---|---|---|---|---|---|---|---|---|---|---|
| | 1 | 2 | 3 | 4 | 5 | 6 | 7 | 8 | 9 | 10 |
| Choice A | I | L | L | M | G | W | K | C | S | F |
| Choice B | V | A | I | P | H | N | R | T | A | Y |
| Protein Sequence | V | A | L | P | G | W | K | T | S | F |
| Model Sequence | −1 | −1 | +1 | −1 | +1 | +1 | +1 | −1 | +1 | +1 |

With this coding scheme, the linear model used to associate protein sequences with activity can be written as follows:

$$y = c_1 x_1 + c_2 x_2 + c_3 x_3 \ldots + c_n x_n + \ldots + c_N x_N + c_0 \quad (3)$$

where y is the response (activity), $c_n$ the regression coefficient for the residue choice at position n, x the dummy variable coding for the residue choice (+1/−1) at position n, and c0 the mean value of the response. This form of the model assumes there are no interactions between the variable residues—each residue choice contributes independently to the overall fitness of the protein.

The non-linear model includes a certain number of (as yet undetermined) cross-product terms to account for interactions between residues:

$$y = c_1 x_1 + c_2 x_2 + c_3 x_3 + \ldots c_n x_n + c_{1,2} x_1 x_2 + c_{1,3} x_1 x_3 + c_{2,3} x_2 x_3 + \ldots + c_0 \quad (4)$$

where the variables are the same as those in Eq. (3) but now there are non-linear terms, e.g., $c_{1,2}$ is the regression coefficient for the interaction between variable positions 1 and 2.

In order to assess the performance of the linear and non-linear models a synthetic data source known as the NK landscape (Kauffman, 1993) was used. As mentioned, N is the number of variable positions in a simulated protein and K is the epistatic coupling between residues. The synthetic data set was generated only in silico.

This data set was used to generate an initial training set with S=40 synthetic samples, N=20 variable positions and K=1 (to reiterate, for K=1 each variable position is functionally coupled to one other variable position). In generating the randomized proteins, each variable position had an equal probability of containing the dummy variable +1 or −1. The residue-residue interactions (represented by cross-products) and actual activities are known for each member of the synthetic training set. Another V=100 samples were generated for use in validation. Again, the residue-residue interactions and activities are known for each member of the validation set.

Figure 3A:
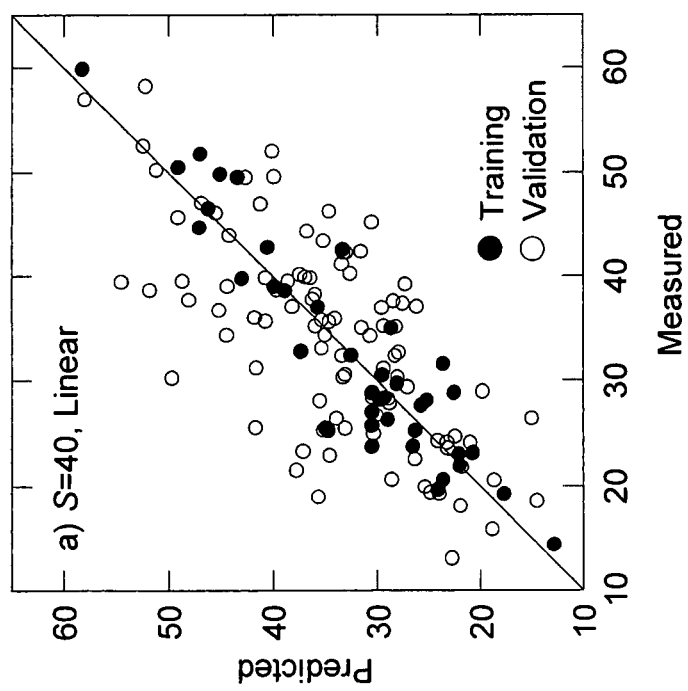
FIGS. 3A-3F are graphs showing examples of this invention in which the predictive capabilities of certain linear and non-linear models are compared.

The training sets were used to construct both linear and non-linear models using the methods described above. Some non-linear models were generated with selection of the cross-product terms (using a genetic algorithm as described above) and other non-linear models were generated without selection of such terms. For the training set size of S=40, the linear model was capable of correlating the measured and predicted values reasonably well, but demonstrated weaker correlation when validated against data not seen in the training set (see FIG. 3A). As shown, the dark data points represent the cross-validated predictions made by a linear model based on the other 39 data points in the training set and predicting the single held out data point. Thus there are actually 40 slightly different models represented by the dark data points. The light data points represent the predictions made by a single model constructed from the 40 training samples and used to predict the validation samples V, none of which were seen in the original training set. The use of the validation set then gives a good measure of the true predictive capacity of the model, as opposed to the cross validated training set, which can suffer from the model overfit problem especially for the non-linear cases described below.

Figure 3B:
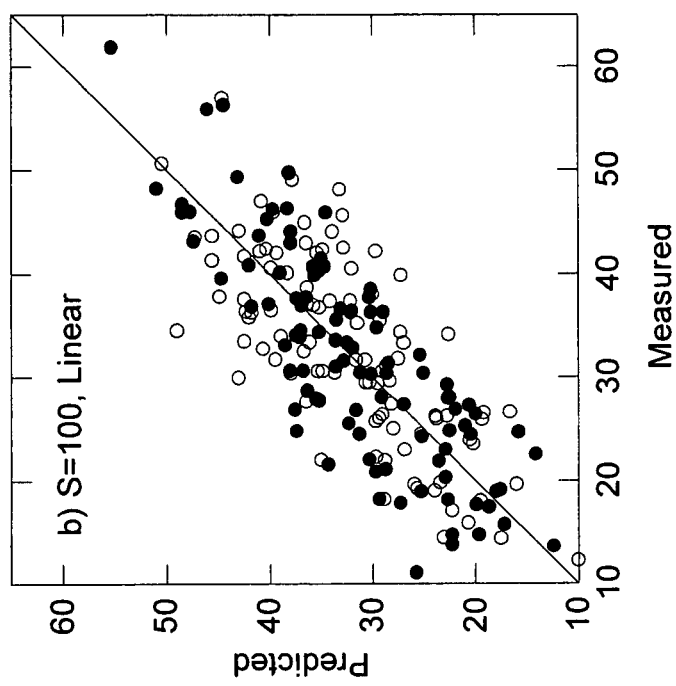

This result for S=40 is interesting considering the linear model was used to model a non-linear fitness landscape. In this case, the linear model could, at best, capture the average contribution to fitness for the choice of a given residue. With enough of these average contributions taken together, the linear model could roughly predict the measured response. The validation results for the linear model were marginally better when the training size was increased to S=100 (see FIG. 3B). Then tendency of relatively simple models to underfit data is known as bias.

Figure 3C:
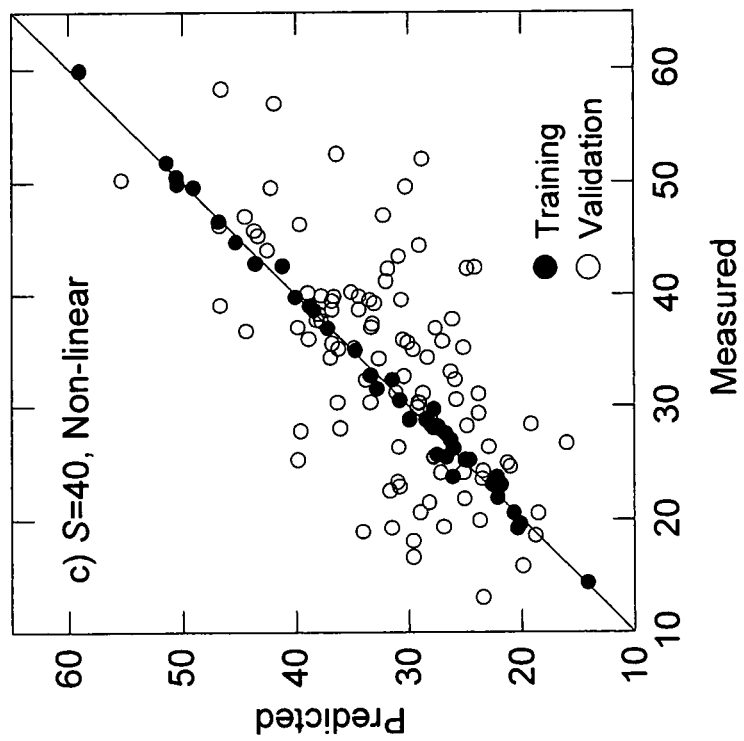
Figure 3D:
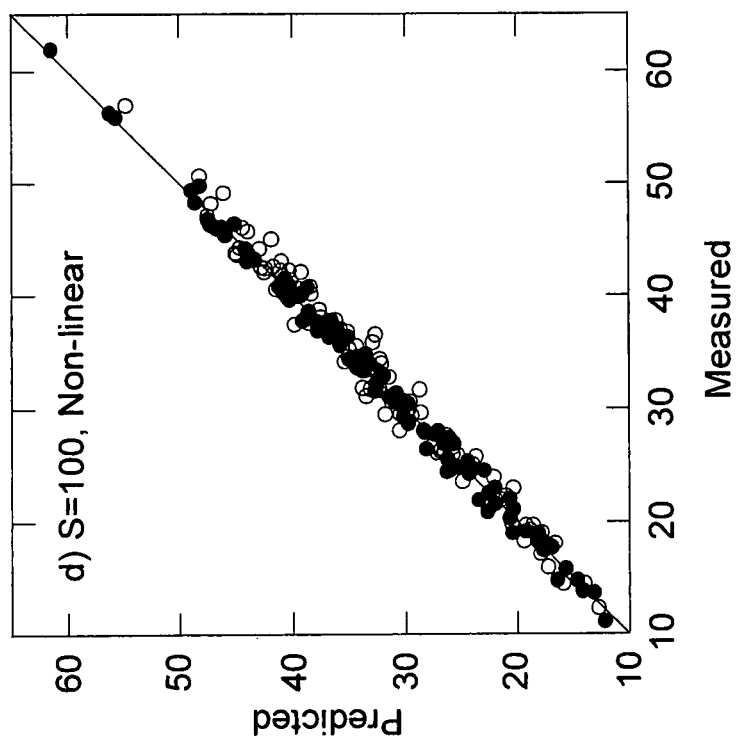

When the non-linear model was trained using only S=40 samples (and 20 non-linear cross-product terms were selected using a genetic algorithm as described above), the correlation with training set members was excellent (see FIG. 3C). Unfortunately, the model contained limited predictive power outside the training set, as evidenced by its limited correlation with measured values in the validation set. This non-linear model, with many potential variables (210 possible), and limited training data to facilitate identification of the proper cross-product terms, was able to essentially just memorize the data set it was trained on. This tendency of high complexity models to overfit the data is known as the variance. The bias-variance tradeoff represents a fundamental problem in machine learning and some form of validation is almost always required to address it when dealing with new or uncharacterized machine learning problems. Satisfyingly, for the larger training set (S=100) the non-linear model performed exceedingly well for both the training prediction and, more importantly, the validation prediction (see FIG. 3D). The validation predictions were so good that most of the data points are obscured by the dark circles use to plot the training set.

Figure 3E:
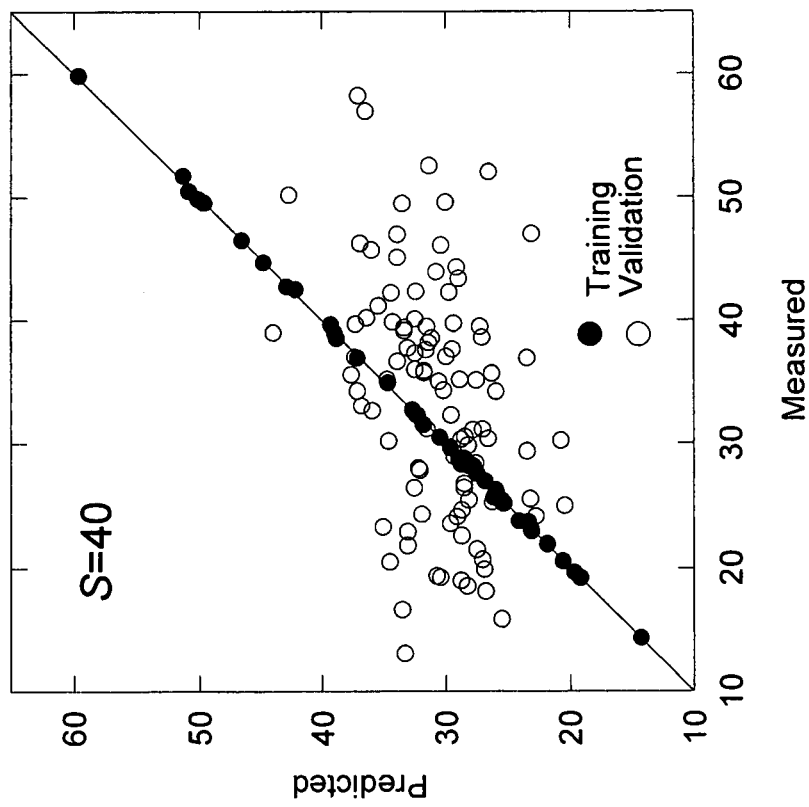
Figure 3F:
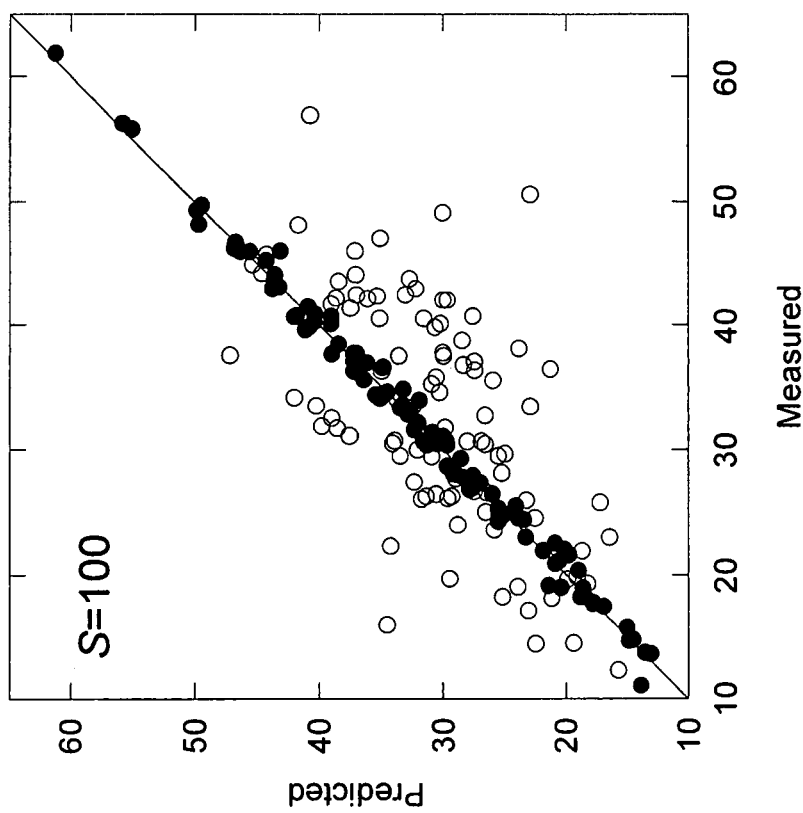

For comparison, FIGS. 3E and 3F show the performance of non-linear models prepared without careful selection of the cross-product terms. Unlike the models in FIGS. 3C and 3D, every possible cross-product term was chosen (i.e., 190 cross-product terms for N=20). As can be seen, the ability to predict validation set activity is relatively poor compared that of the non-linear models generated with selection of cross-product terms. This is a manifestation of overfitting.

iii) Generating an Optimized Protein Variant Library by Modifying Model-Predicted Sequences Rather than simply synthesizing the single best-predicted protein one may generate a combinatorial library of proteins based on a sensitivity analysis of the best protein to changes in the residue choices at each location. The more sensitive a given residue choice is for the predicted protein, the greater the predicted fitness change will be. One can rank these sensitivities from highest to lowest and use the sensitivity scores to create combinatorial protein libraries in subsequent rounds by incorporating those residues based on sensitivity. For a linear model the sensitivity may be identified by simply considering the size of the coefficient associated with a given residue term in the model. For the non-linear model, this will not be possible. Instead the residue sensitivity may be determined by using the model to calculate changes in activity when a single residue is varied in the "best" predicted sequence.

Residues may be considered in the order in which they are ranked. For each residue under consideration, the process determines whether to "toggle" that residue. The term "toggling" refers to the introduction of multiple amino acid residue types into a specific position in the sequences of protein variants in the optimized library. For example, serine may appear in position 166 in one protein variant, whereas phenylalanine may appear in position 166 in another protein variant in the same library. Amino acid residues that did not vary between protein variant sequences in the training set typically remain fixed in the optimized library.

An optimized protein variant library can be designed such that all of the identified "high" ranking regression coefficient residues are fixed, and the remaining lower ranking regression coefficient residues are toggled. The rationale for this being that one should search the local space surrounding the 'best' predicted protein. Note that the starting point "backbone" in which the toggles are introduced may be the best protein predicted by a model or an already validated 'best' protein from a screened library.

In an alternative approach, at least one or more, but not all of the high-ranking regression coefficient residues identified may be fixed in the optimized library, and the others toggled. This approach is recommended if it is desired not to drastically change the context of the other amino acid residues by incorporating too many changes at one time. Again, the starting point for toggling may be the best set of residues as predicted by the model or a best validated protein from an existing library. Or the starting point may be an "average" clone that models well. In this case, it may be desirable to toggle the residues predicted to be of higher importance. The rationale for this being that one should explore a larger space in search for activity hills previously omitted from the sampling. This type of library is typically more relevant in early rounds as it generates a more refined picture for subsequent rounds.

Alternatives to the above methodology involve different procedures for using residue importance (rankings) in determining which residues to toggle. In one such alternative, higher ranked residue positions are more aggressively favored for toggling. The information needed in this approach includes the sequence of a best protein from the training set, a PLS or PCR predicted best sequence, and a ranking of residues from the PLS or PCR model. The "best" protein is a wet-lab validated "best" clone in the dataset (clone with the highest measured function that still models well, i.e., falls relatively close to the predicted value in cross validation). The method compares each residue from this protein with the corresponding residue from a "best predicted" sequence having the highest value of the desired activity. If the residue with the highest load or regression coefficient is not present in the 'best' clone, the method introduces that position as a toggle position for the subsequent library. If the residue is present in the best clone, the method will not treat the position as a toggle position, and it will move the next position in succession. The process is repeated for various residues, moving through successively lower load values, until the library is of sufficient size is generated.

The number of regression coefficient residues to retain, and number of regression coefficient residues to toggle, can be varied. Factors to consider include the desired library size, the magnitude of difference between regression coefficients, and the degree to which nonlinearity is thought to exist—retaining residues with small (neutral) coefficients may uncover important nonlinearities in subsequent rounds of evolution. Typical optimized protein variant libraries of the present invention contain about $2^N$ protein variants, where N represents the number of positions that are toggled between two residues. Stated another way, the diversity added by each additional toggle doubles the size of the library such that 10 toggle positions produces ~1,000 clones (1,024), 13 positions~10,000 clones (8,192) and 20 positions~1,000,000 clones (1,048,576). The appropriate size of library depends on factors such as cost of screen, ruggedness of landscape, preferred percentage sampling of space etc. In some cases, it has been found that a relatively large number of changed residues produces a library in which an inordinately large percentage of the clones are non-functional. Therefore for some applications, it may be recommended that the number of residues for toggling ranges from about 2 to about 30; i.e., the library size ranges from between about 4 and $2^{30}$~$10^9$ clones.

In practice, one can pursue various subsequent round library strategies at the same time, with some strategies being more aggressive (fixing more "beneficial" residues) and other strategies being more conservative (fixing fewer "beneficial" residues in the hopes of exploring the space more thoroughly).

It may be desirable to identify and preserve groups or residues or "motifs" that occur in most naturally occurring or otherwise successful peptides. For example, it may be found that Ile at variable position 3 is always coupled with Val at variable position 11 in naturally occurring peptides. It has been found that such residue groups can be important to preserving activity in the peptide. Hence, in one embodiment, preservation of such groups is required in any toggling strategy. In other words, the only accepted toggles are those that preserve a particular grouping in the base protein or those that generate a different grouping that is also found in active proteins. In the latter case it will be necessary to toggle two or more residues.

In varied approaches, a wet-lab validated 'best' (or one of the few best) protein in the current optimized library (i.e., a protein with the highest, or one of the few highest, measured function that still models well, i.e., falls relatively close to the predicted value in cross validation) may serve as a backbone where various schemes of changes are incorporated. In another approach, a wet-lab validated 'best' (or one of the few best) protein in the current library that may not model well may serve as a backbone where various schemes of changes are incorporated. In other approaches, a sequence predicted by the sequence activity model to have the highest value (or one of the highest values) of the desired activity may serve as the backbone. In these approaches, the dataset for the "next generation" library (and possibly a corresponding model) is obtained by changing residues in one or a few of the best proteins. In one embodiment, these changes comprise a systematic variation of the residues in the backbone. In some cases, the changes comprise various mutagenesis, recombination and/or subsequence selection techniques. Each of these may be performed in vitro, in vivo, or in silico.

While the optimal sequence is predicted by a linear model can be identified by inspection as described above, the same is not true of a non-linear model. Certain residues appear in both linear and cross product terms and their overall affect on activity in the context of many possible combinations of other residues can present a daunting problem.

As with selection of cross product terms for a non-linear model, the optimal sequence predicted by a non-linear model can be identified by testing all possible sequences with the model (assuming sufficient computational resources) or a searching algorithm such as a genetic algorithm. One exemplary genetic algorithm will now be described.

In this algorithm, the fitness function is simply the non-linear model's prediction of activity. In a specific example, an elitism rate of about 5-10% is employed. Selection of parents for mating involves a linear weighted fitness operation. The selected parents provide ordered sets of residues and a uniform cross over operation is employed. The best computer generated protein is picked after no improvement is seen for at least 15 generations.

The information contained in the computer-evolved proteins identified as described above can be used to synthesize novel proteins in the lab and test them on physical assays. An accurate in silico representation of the real wet lab fitness function, allows researchers to reduce the number of cycles of evolution or the number variants needed to screen in the lab. Optimized protein variant libraries can be generated using the recombination methods described herein, or alternatively, by gene synthesis methods, followed by in vivo or in vitro expression. After, the optimized protein variant libraries are screened for desired activity, they may be sequenced. As indicated above in the discussion of FIG. 1, the activity and sequence information from the optimized protein variant library can be employed to generate another sequence activity model from which a further optimized library can be designed, using the methods described herein. In one approach, all proteins from this new library are used as part of the dataset.

iv) Alternative Modelling Options

Multiple other variations on the above approach are within the scope of this invention. As one example, the $x_{ij}$ variables are representations of the physical or chemical properties of amino acids—rather than the exact identities of the amino acids themselves (leucine versus valine versus proline, . . . ). Examples of such properties include lipophilicity, bulk, and electronic properties (e.g., formal charge, van der Waals surface area associated a partial charge, etc.). To implement this approach, the $x_{ij}$ values representing amino acid residues can be presented in terms of their properties or principal components constructed from the properties.

In another variation, the $x_{ij}$ variables represent nucleotides, rather than amino acid residues. The goal is to identify nucleic acid sequences that encode proteins for a protein variant library. By using nucleotides rather than amino acids, one can optimize on parameters other than merely specific activity. For example, protein expression in a particular host or vector may be a function of nucleotide sequence. Two different nucleotide sequences may encode a protein having one amino acid sequence, but one of the nucleotide sequences expresses greater quantities of protein and/or expresses the protein in a more active state. By using nucleotide sequences rather than amino acid sequences, the methods of this invention can optimize for expression properties, for example, as well as specific activity.

In a specific embodiment, the nucleotide sequence is represented as codons. Models may employ codons as the atomic unit of a nucleotide sequence such that the predicted activities are a function of various codons in the nucleotide sequence. Each codon together with its position in the overall nucleotide sequence serves as an independent variable for generating sequence activity models. Note that different codons for given amino acid express differently in a given organism. More specifically, each organism has a preferred codon, or distribution of codon frequencies, for a given amino acid. By using codons as the independent variables, the invention accounts for these preferences. Thus, the invention can be used to generate a library of expression variants (e.g., where "activity" includes expression level from a particular host organism).

An outline of a particular method includes the following operations: (a) receiving data characterizing a training set of a protein variant library; (b) from the data, developing a non-linear sequence activity model that predicts activity as a function of nucleotide types and corresponding position in the nucleotide sequence; (c) using the sequence activity model to rank positions in a nucleotide sequence and/or nucleotide types at specific positions in the nucleotide sequence in order of impact on the desired activity; and (d) using the ranking to identify one or more nucleotides, in the nucleotide sequence, that are to be varied or fixed in order to impact the desired activity. As indicated, the nucleotides to be varied are preferably codons encoding particular amino acids.

Other variations of the above approach involve use of different techniques for ranking residues or otherwise characterizing them in terms of importance. With linear models, the magnitudes of regression coefficients were used to rank residues. Residues having coefficients with large magnitudes (e.g., 166 Ile) were viewed as high-ranking residues. This characterization was used to decide whether or not to vary a particular residue in the generation of a new, optimized library of protein variants. For non-linear models, the sensitivity analysis was more complex.

PLS and other techniques provide other information, beyond regression coefficient magnitude, that can be used to rank specific residues or residue positions. Techniques such as PLS and Principle Component Analysis (PCA) or PCR provide information in the form of principle components or latent vectors. These represent directions or vectors of maximum variation through multi-dimensional data sets such as the protein sequence-activity space employed in this invention. These latent vectors are functions of the various sequence dimensions; i.e., the individual residues or residue positions that comprise the protein sequences of the variant library used to construct the training set. A latent vector will therefore comprise a sum of contributions from each of the residue positions in the training set. Some positions will contribute more strongly to the direction of the vector. These will be manifest by relatively large "loads," i.e., the coefficients used to describe the vector. As a simple example, a training set may be comprised of tripeptides. The first latent vector will typically have contributions from all three residues.

$$\text{Vector } 1 = a1(\text{residue position } 1) + a2(\text{residue position } 2) + a3(\text{residue position } 3)$$

The coefficients, a1, a2, and a3, are the loads. Because these reflect the importance of the corresponding residue positions to variation in the dataset, they can be used to rank the importance of individual residue positions for purposes of "toggling" decisions, as described above. Loads, like regression coefficients, may be used to rank residues at each toggled position. Various parameters describe the importance of these loads. Some such Variable Importance in Projection (VIP) make use of a load matrix, which is comprised of the loads for multiple latent vectors taken from a training set. In Variable Importance for PLS Projection, the importance of the ith variable (e.g., residue position) is computed by calculating VIP (variable importance in projection). For a given PLS dimension, a, $(VIN)_{ak}^2$ is equal to the squared PLS weight $(w_{ak})^2$ of a variable multiplied by the percent explained variability in y (dependent variable, e.g., certain function) by that PLS dimension. $(VIN)_{ak}^2$ is summed over all PLS dimensions (components). VIP is then calculated by dividing the sum by the total percent variability in y explained by the PLS model and multiplying by the number of variables in the model. Variables with large VIP, larger than 1, are the most relevant for correlating with a certain function (y) and hence highest ranked for purposes of making toggling decisions.

Another embodiment of the invention employs techniques that rank residues not simply by the magnitudes of their predicted contributions to activity, but by the confidence in those predicted contributions as well. In some cases the researcher will be concerned with spurious values of the coefficients or principal components.

In a more statistically rigorous approach, the ranking is based on a combination of magnitude and distribution. Coefficients with both high magnitudes and tight distributions give the highest ranking. In some cases, one coefficient with a lower magnitude than another may be given a higher ranking by virtue of having less variation. Thus, some embodiments of the invention rank residues or nucleotides based on both magnitude and standard deviation or variance. Various techniques can be used to accomplish this. One of these, a bootstrap p-value approach, will now be described.

Figure 4:
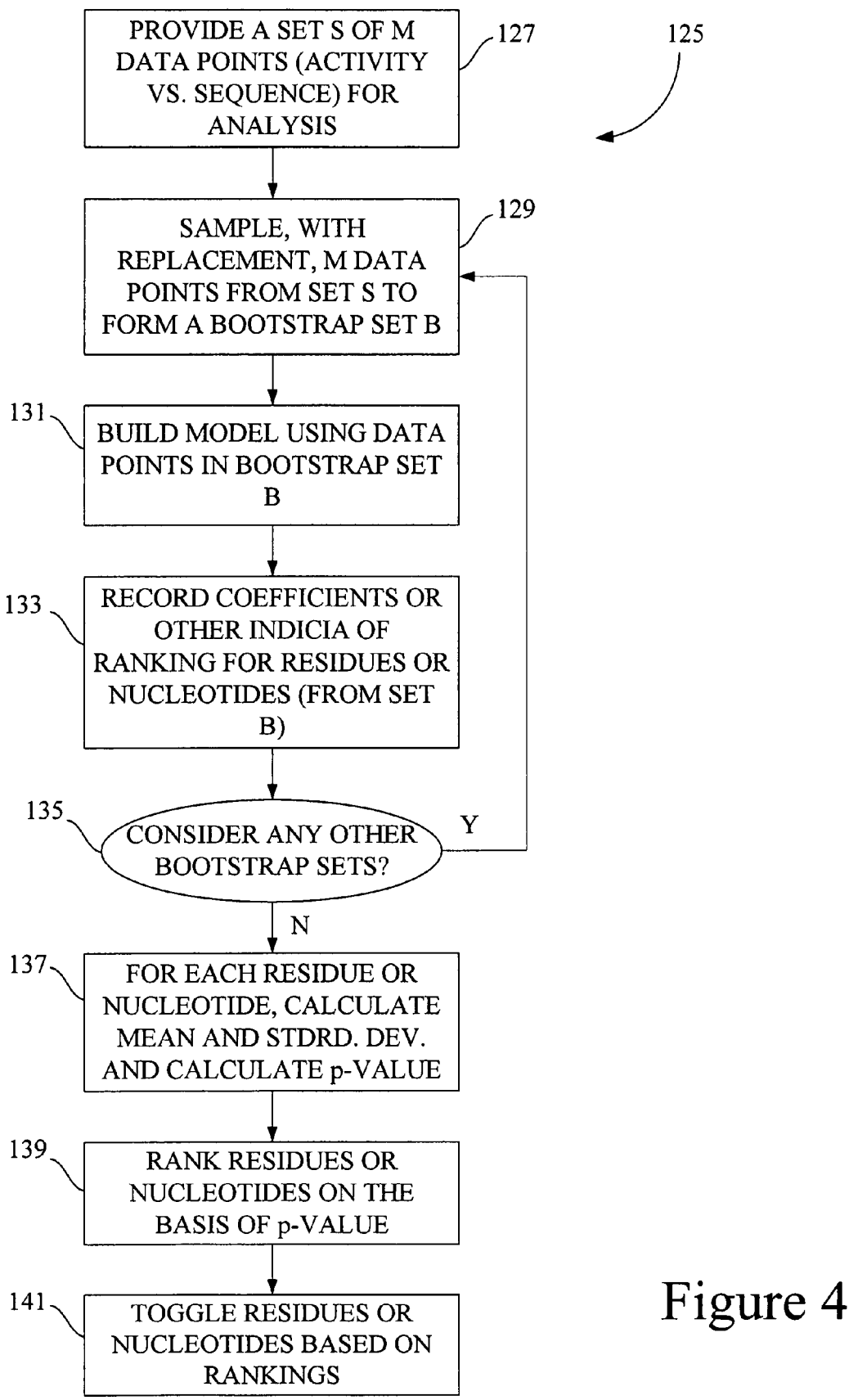
FIG. 4 is a flow chart depicting a bootstrap p-value method of generating protein variant libraries in accordance with an embodiment of this invention.

An example of a method that employs a bootstrap method is depicted in FIG. 4. As shown there, a method 125 begins at a block 127 where an original data set S is provided. This may be a training set as described above. For example, it may be generated by systematically varying the individual residues of a starting sequence in any one of the manners described above. In the example of method 125, the data set S has M different data points (activity and sequence information collected from amino acid or nucleotide sequences) for use in the analysis.

From data set S, various bootstrap sets B are created. Each of these is obtained by sampling, with replacement, from set S to create a new set of M members—all taken from original set S. See block 129. The "with replacement" condition produces variations on the original set S. The new bootstrap set, B, will sometimes contain replicate samples from S. And, it may also lack certain samples originally contained in S.

As an example, consider a set S of 100 sequences. Each bootstrap set B used in the method contains itself 100 sequences. A bootstrap set B is created by randomly selecting each of the 100 member sequences from the 100 sequences in the original set S. Thus, it is possible that some sequences will be selected more than once and others will not be selected at all.

Using the bootstrap set B currently under consideration, the method next builds a model. See block 131. The model may be built as described above, using PLS, PCR, a SVM, genetic programming, etc. This model will provide coefficients or other indicia of ranking for the residues or nucleotides found in the various samples from set B. As shown at a block 133, these coefficients or other indicia are recorded for subsequent use.

Next, at a decision block 135, the method determines whether another bootstrap set should be created. If yes, the method returns to block 129 where a new bootstrap set B is created as described above. If no, the method proceeds to a block 137 discussed below. The decision at block 135 turns on how many different sets of coefficient values are to be used in assessing the distributions of those values. The number of sets B should be sufficient to generate accurate statistics. As an example, 100 to 1000 bootstrap sets are prepared and analyzed. This is represented as about 100 to 1000 passes through blocks 129, 131, and 133 of method 125.

After a sufficient number bootstrap sets B have been prepared and analyzed as described, decision 135 is answered in the negative. As indicated, the method then proceeds to block 137. There a mean and standard deviation of a coefficient (or other indicator generated by the model) is calculated for each residue or nucleotide (including codons) using the coefficient values (e.g., 100 to 1000 of them, one from each bootstrap set). From this information, the method can calculate the t-statistic and determine the confidence interval that the measured value is different from zero. From the t-statistic it calculates the p-value for the confidence interval. In this case, the smaller p-value the more confidence that the measured regression coefficient is different from zero.

Note that the p-value is but one of many different types of characterization that can account for the statistical variation in a coefficient or other indicator of residue importance. Examples include calculating 95 percent confidence intervals for regression coefficients and excluding any regression coefficient for consideration for which 95 percent confidence interval crosses zero line. Basically, any characterization that accounts for standard deviation, variance, or other statistically relevant measure of data distribution can be used. Such characterization preferably also accounts for the magnitude of the coefficients.

A large standard deviation can result from various sources. One source is poor measurements in the data set. Another is a limited representation of a particular residue or nucleotide in the original data set. In this latter case, some bootstrap sets will contain no occurrences of a particular residue or nucleotide. In such cases, the value of the coefficient for that residue will be zero. Other bootstrap sets will contain at least some occurrences of the residue or nucleotide and give a non-zero value of the corresponding coefficient. But the sets giving a zero value will cause the standard deviation of the coefficient to become relatively large. This reduces the confidence in the coefficient value and results in a lower rank. But this is to be expected, given that there is relatively little data on the residue or nucleotide in question.

Next, at a block 139, the method ranks the regression coefficients (or other indicators) from lower (best) p-value to highest (worst) p-value. This ranking correlates highly with the absolute value of the regression coefficients themselves, owing to the fact that the larger the absolute value, the more standard deviations removed from zero. Thus, for a given standard deviation, the p-value becomes smaller as the regression coefficient becomes larger. However, the absolute ranking will not always be the same with both p-value and pure magnitude methods, especially when relatively few data points are available to begin with in set S.

Finally, as shown at a block 141, the method fixes and toggles certain residues based on the rankings observed in the operation of block 139. This is essentially the same use of rankings described above for other embodiments. In one approach, the method fixes the best residues (now those with the lowest p-values) and toggles the others (those with highest p-values).

This method 125 has been shown in silico to perform well. Moreover, the p-value ranking approach naturally deals with single or few instance residues: the p-values will generally be higher (worse) because in the bootstrap process, those residues that did not appear often in the original data set will be less likely to get picked up at random. Even if their coefficients are large, their variability (measured in standard deviations) will be quite high as well. Intuitively, this is the desired result, since those residues that are not well represented (either have not seen with sufficient frequency or have lower regression coefficients) may be good candidates for toggling in the next round of library design.

III. Digital Apparatus and Systems

As should be apparent, embodiments of the present invention employ processes acting under control of instructions and/or data stored in or transferred through one or more computer systems. Embodiments of the present invention also relate to apparatus for performing these operations. Such apparatus may be specially designed and/or constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein. In some cases, however, it may be more convenient to construct a specialized apparatus to perform the required method operations. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, magnetic tape; optical media such as CD-ROM devices and holographic devices; magneto-optical media; semiconductor memory devices, and hardware devices that are specially configured to store and perform program instructions, such as read-only memory devices (ROM) and random access memory (RAM), and sometimes application-specific integrated circuits (ASICs), programmable logic devices (PLDs) and signal transmission media for delivering computer-readable instructions, such as local area networks, wide area networks, and the Internet. The data and program instructions of this invention may also be embodied on a carrier wave or other transport medium (e.g., optical lines, electrical lines, and/or airwaves).

Examples of program instructions include both low-level code such as produced by a compiler, and files containing higher level code that may be executed by the computer using an interpreter. Further, the program instructions include machine code, source code and any other code that directly or indirectly controls operation of a computing machine in accordance with this invention. The code may specify input, output, calculations, conditionals, branches, iterative loops, etc.

Figure 5:
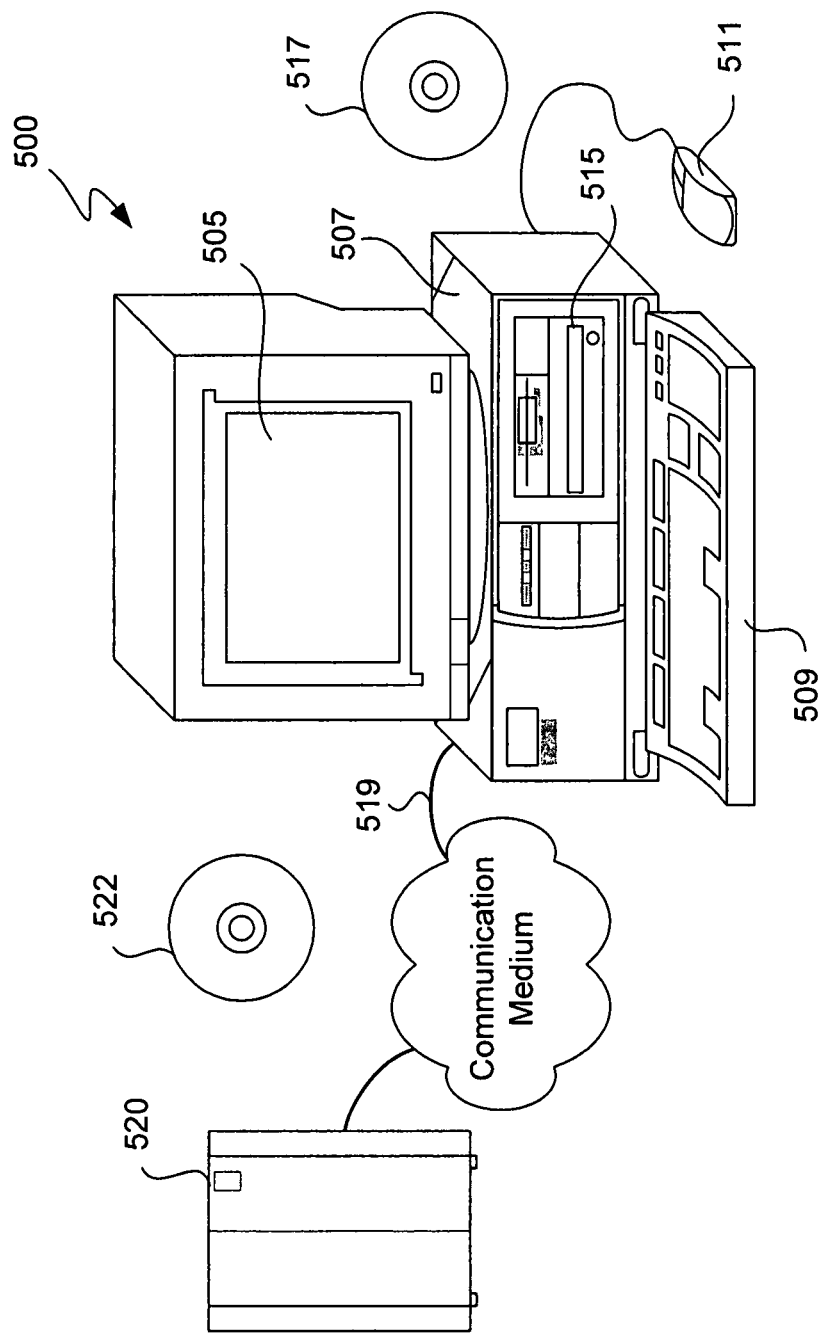
FIG. 5 is a schematic of an example digital device.

In one example, code embodying methods of the invention are embodied in a fixed media or transmissible program component containing logic instructions and/or data that when loaded into an appropriately configured computing device causes the device to perform a genetic operator on one or more character string. FIG. 5 shows an example digital device 500 that should be understood to be a logical apparatus that can read instructions from media 517, network port 519, user input keyboard 509, user input 511 or other inputting means. Apparatus 500 can thereafter use those instructions to direct statistical operations in data space, e.g., to construct one or more data set (e.g., to determine a plurality of representative members of the data space). One type of logical apparatus that can embody the invention is a computer system as in computer system 500 comprising CPU 507, optional user input devices keyboard 509, and GUI pointing device 511, as well as peripheral components such as disk drives 515 and monitor 505 (which displays GO modified character strings and provides for simplified selection of subsets of such character strings by a user. Fixed media 517 is optionally used to program the overall system and can include, e.g., a disk-type optical or magnetic media or other electronic memory storage element. Communication port 519 can be used to program the system and can represent any type of communication connection.

The invention can also be embodied within the circuitry of an application specific integrated circuit (ASIC) or programmable logic device (PLD). In such a case, the invention is embodied in a computer readable descriptor language that can be used to create an ASIC or PLD. The invention can also be embodied within the circuitry or logic processors of a variety of other digital apparatus, such as PDAs, laptop computer systems, displays, image editing equipment, etc.

IV. Other Embodiments

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for identifying amino acid residues for variation in a protein variant library in order to affect a desired activity, said method comprising:
 (a) receiving data characterizing a training set of a protein variant library, wherein the data provides activity and an amino acid sequence for each protein variant in the training set;
 (b) from the data, developing a sequence-activity model for predicting activity as a function of multiple independent variables,
  wherein
  the sequence activity model comprises a plurality of linear terms and one or more non-linear terms,
  the linear and non-linear terms are separated by plus or minus signs,
  each linear term comprises the product of a coefficient and a bit-value independent variable, wherein the coefficient of the linear term indicates the relative impact on activity by the bit-value independent variable, and wherein the bit-value independent variable specifies the presence or absence of only one particular amino acid residue of a specific residue type at a specific sequence position, and
  each non-linear term is a cross-product term comprising the product of a coefficient and two or more bit-value independent variables, wherein the coefficient of the non-linear term indicates the relative impact on activity by the interaction of the two or more bit-value independent variables, and wherein each of the two or more bit-value independent variables specifies the presence or absence of a particular residue of a specific residue type at a specific sequence position; and (c) using the sequence-activity model to identify one or more amino acid residues at specific positions for varying or fixing to impact the desired activity, wherein operations (a)-(c) are performed by executing instructions on a computer system programmed to perform said operations.

2. The method of claim 1, wherein developing said sequence-activity model comprises selecting one or more cross-product terms from a group of potential cross-product terms.

3. The method of claim 2, wherein selecting the one or more cross-product terms comprises running a genetic algorithm to select one or more cross-product terms based upon the predictive ability of various models employing different cross-product terms.

4. The method of claim 1, wherein the protein variants in the protein variant library have systematically varied sequences.

5. The method of claim 4, further comprising performing DOE to identify the systematically varied sequences.

6. The method of claim 1, wherein the sequence activity model is used to identify one or more amino acid residues that are to remain fixed in a new protein variant library.

7. The method of claim 1, wherein the protein variant library comprises naturally occurring proteins or proteins derived therefrom.

8. The method of claim 7, wherein the naturally occurring proteins comprise proteins that are encoded by members of a single gene family.

9. The method of claim 1, wherein the protein variant library comprises proteins that are obtained by using a recombination-based diversity generation mechanism.

10. The method of claim 1, wherein the sequence activity model is a regression model.

11. The method of claim 1, wherein using the sequence activity model to identify one or more amino acid residues further comprises identifying sequences for use in a recombination-based diversity generation mechanism, wherein said sequences comprise variations in the one or more amino acid residues identified in (c).

12. The method of claim 1, wherein using the sequence activity model comprises identifying a sequence predicted by the model to have a highest value of the desired activity.

13. The method of claim 1, wherein using the sequence activity model to identify one or more amino acid residues comprises using the sequence activity model to rank residue positions in order of impact on the desired activity.

14. The method of claim 1, wherein using the model comprises using the model as a fitness function in a genetic algorithm.

15. The method of claim 14, wherein the genetic algorithm is employed to select a sequence predicted by the model to have a highest value of the desired activity.

16. The method of claim 1, wherein using the sequence activity model to identify one or more amino acid residues at specific positions comprises identifying one or more sequences for use in generating a new protein variant library.

17. The method of claim 16, wherein the one or more sequences for use in generating the new protein variant library are oligonucleotide sequences encoding variations of the one or more identified amino acid residues.

18. The method of claim 17, wherein the oligonucleotide sequences encode at least a portion of (i) a naturally occurring parent protein having the highest activity among naturally occurring parent proteins, or (ii) a sequence predicted by the sequence activity model to have the highest activity.

19. The method of claim 16, further comprising developing a new sequence activity model using activity and sequence data characterizing the new protein variant library.

20. The method of claim 1, wherein the one or more amino acid residues identified in (c) are identified in a reference sequence predicted using the sequence activity model or a reference sequence that describes a member of the protein variant library.

21. The method of claim 1, wherein the training set of a protein variant library comprises proteins that were obtained by performing DNA fragmentation-mediated recombination or a synthetic oligonucleotide-mediated recombination on nucleic acids encoding all or part of one or more naturally occurring parent proteins.

22. The method of claim 1, further comprising:

(d) generating a new protein variant library containing one or more new protein variants having amino acid sequences encoded by nucleic acids in which the identified nucleotides are varied or fixed in order to impact the desired activity;

(e) assaying the new protein variant library to provide activity information for members of the new protein variant library to select a protein for production; and (f) producing the protein selected in (e).

23. A computer program product comprising a non-transitory machine readable memory on which is provided program instructions for identifying amino acid residues for variation in a protein variant library in order to affect a desired activity, said program instructions comprising:

(a) code for receiving data characterizing a training set of a protein variant library, wherein the data provides activity and an amino acid sequence for each protein variant in the training set;

(b) code for developing, from the data, a sequence-activity model for predicting activity as a function of multiple independent variables, wherein the sequence activity model comprises a plurality of linear terms and one or more non-linear terms, the linear and non-linear terms are separated by plus or minus signs, each linear term comprises the product of a coefficient and a bit-value independent variable, wherein the coefficient of the linear term indicates the relative impact on activity by the bit-value independent variable, and wherein the bit-value independent variable specifies the presence or absence of only one particular amino acid residue of a specific residue type at a specific sequence position, and each non-linear term is a cross-product term comprising the product of a coefficient and two or more bit-value independent variables, wherein the coefficient of the non-linear term indicates the relative impact on activity by the interaction of the two or more bit-value independent variables, and wherein each of the two or more bit-value independent variables specifies the presence or absence of a particular residue of a specific residue type at a specific sequence position; and (c) code for using the sequence-activity model to identify one or more amino acid residues at specific positions for varying or fixing to impact the desired activity.

24. The computer program product of claim 23, wherein the code for developing said sequence-activity model comprises code for selecting one or more cross-product terms from a group of potential cross-product terms.

25. The computer program product of claim 24, wherein the code for selecting the one or more cross-product terms comprises code for running a genetic algorithm to select one or more cross-product terms based upon the predictive ability of various models employing different cross-product terms.

26. The computer program product of claim 23, wherein the sequence activity model is a regression model.

27. The computer program product of claim 23, wherein the code for using the sequence activity model to identify one or more amino acid residues further comprises code for identifying sequences for use in a recombination-based diversity generation mechanism, wherein said sequences comprise variations in the one or more amino acid residues identified in (c).

28. The computer program product of claim 23, wherein the code for using the sequence activity model comprises code for identifying a sequence predicted by the model to have a highest value of the desired activity.

29. The computer program product of claim 23, wherein the code for using the sequence activity model to identify one or more amino acid residues comprises code for using the sequence activity model to rank residue positions in order of impact on the desired activity.

30. The computer program product of claim 23, wherein the code for using the sequence activity model to identify one or more amino acid residues at specific positions comprises code for identifying one or more sequences for use in generating a new protein variant library.

31. The computer program product of claim 30, wherein the one or more sequences for use in generating the new protein variant library are oligonucleotide sequences encoding variations of the one or more identified amino acid residues.

* * * * *